(12) United States Patent
Chung et al.

(10) Patent No.: US 10,436,776 B2
(45) Date of Patent: Oct. 8, 2019

(54) METHODS AND SYSTEMS FOR SELECTION OF DETECTION AREA

(71) Applicant: PLEXBIO CO., LTD., Taipei (TW)

(72) Inventors: Yao-Kuang Chung, New Taipei (TW); Chia-En Tai, Taipei (TW); Liang Han Chang, New Taipei (TW)

(73) Assignee: PLEXBIO CO., LTD., Taipei (TW)

( * ) Notice: Subject to any disclaimer, the term of this patent is extended or adjusted under 35 U.S.C. 154(b) by 269 days.

(21) Appl. No.: 15/358,024

(22) Filed: Nov. 21, 2016

(65) Prior Publication Data

US 2017/0146545 A1    May 25, 2017

Related U.S. Application Data

(60) Provisional application No. 62/258,388, filed on Nov. 20, 2015.

(51) Int. Cl.
*G01N 33/543* (2006.01)
*G06T 7/11* (2017.01)

(52) U.S. Cl.
CPC .............. *G01N 33/543* (2013.01); *G06T 7/11* (2017.01); *G06T 2207/30072* (2013.01)

(58) Field of Classification Search
USPC ........................................................ 235/494
See application file for complete search history.

(56) References Cited

U.S. PATENT DOCUMENTS 7,858,307 B2    12/2010 Ho
7,871,770 B2    1/2011 Ho
(Continued)

FOREIGN PATENT DOCUMENTS

CN    1271410 C    8/2006
CN    102246037 B    5/2014
(Continued)

OTHER PUBLICATIONS

Tsao, et al., Unpublished U.S. Appl. No. 16/332,271, filed Mar. 11, 2019, titled "Methods and Systems for Multiplex Assays", (U.S. Patent Application is not submitted herewith pursuant to the waiver of 37 C.F.R. § 1.98(a)(2)(iii) issued by the Office on Sep. 21, 2004).

(Continued)

*Primary Examiner* — Michael G Lee
*Assistant Examiner* — David Tardif
(74) *Attorney, Agent, or Firm* — Morrison and Foerster LLP

(57) ABSTRACT

Provided herein are methods, systems, devices, and computer-readable storage media for selecting a detection area for a well (e.g., as part of an assay plate) comprising a plurality of encoded microcarriers. In some aspects, selecting the detection area includes obtaining one or more images of the well; calculating a center of the well according to a two-dimensional coordinate system; assigning a position, according to the two-dimensional coordinate system, of a first encoded microcarrier from the plurality; determining whether a distance between the position of the first encoded microcarrier and the center of the well according to the two-dimensional coordinate system exceeds a threshold distance; and including in the detection area one or more microcarriers whose distance from the center of the well does not exceed the threshold distance, while excluding those whose distance from the center of the well exceeds the threshold.

17 Claims, 13 Drawing Sheets

(56) References Cited

U.S. PATENT DOCUMENTS

| | | | |
|---|---|---|---|
| 8,148,139 B2 | 4/2012 | Ho | |
| 8,232,092 B2 | 7/2012 | Ho et al. | |
| 8,610,848 B2 | 12/2013 | Shim et al. | |
| 8,939,376 B1 | 1/2015 | De Smedt et al. | |
| 8,967,483 B2 | 3/2015 | De Smedt et al. | |
| 9,040,463 B2 | 5/2015 | Demierre et al. | |
| 9,063,044 B2 | 6/2015 | Kao et al. | |
| 9,255,922 B2 | 2/2016 | Ho et al. | |
| 10,019,815 B2 | 7/2018 | Chung et al. | |
| 10,302,640 B2 | 5/2019 | Tsao et al. | |
| 2003/0156763 A1* | 8/2003 | Soderman | G01N 21/6402 382/262 |
| 2006/0097056 A1 | 5/2006 | De Smedt et al. | |
| 2009/0201504 A1 | 8/2009 | Ho et al. | |
| 2010/0075438 A1 | 3/2010 | Ho et al. | |
| 2010/0081215 A1 | 4/2010 | De Geest et al. | |
| 2010/0210477 A1 | 8/2010 | Ho | |
| 2011/0007955 A1 | 1/2011 | Ho et al. | |
| 2011/0111522 A1* | 5/2011 | Zimmerie | A61B 10/007 436/501 |
| 2012/0088691 A1 | 4/2012 | Chen et al. | |
| 2013/0302910 A1 | 11/2013 | Demierre | |
| 2014/0274778 A1 | 9/2014 | Tsao et al. | |
| 2015/0057190 A1 | 2/2015 | De Smedt et al. | |
| 2017/0146545 A1* | 5/2017 | Chung | G06T 7/11 |
| 2017/0160272 A1* | 6/2017 | Tsao | G01N 33/54326 |
| 2018/0179600 A1* | 6/2018 | Hoeppner | C12Q 1/10 |
| 2018/0195113 A1 | 7/2018 | Tsao et al. | |
| 2018/0201983 A1 | 7/2018 | Tsao et al. | |

FOREIGN PATENT DOCUMENTS

| | | | |
|---|---|---|---|
| EP | 1173760 B1 | 6/2005 | |
| EP | 2100143 A1 | 9/2009 | |
| EP | 2179289 A1 | 4/2010 | |
| EP | 2342561 A1 | 7/2011 | |
| EP | 2367633 A1 | 9/2011 | |
| EP | 2484447 A1 | 8/2012 | |
| EP | 2673086 A1 | 12/2013 | |
| EP | 1903337 B1 | 7/2015 | |
| WO | 2000/63695 A1 | 10/2000 | |
| WO | 2008/034275 A1 | 3/2008 | |
| WO | 2009/020506 A1 | 2/2009 | |
| WO | 2009/128938 A1 | 10/2009 | |
| WO | 2010/042745 A1 | 4/2010 | |
| WO | 2010/072011 A1 | 7/2010 | |
| WO | 2011/014879 A2 | 2/2011 | |
| WO | 2012/106827 A1 | 8/2012 | |
| WO | 2014/031997 A1 | 2/2014 | |
| WO | 2014/144016 A1 | 9/2014 | |
| WO | 2016/198954 A1 | 12/2016 | |

OTHER PUBLICATIONS

Braeckmans et al., "Encoding Microcarriers: Present and Future Technologies", Nature Reviews Drug Discovery, vol. 1, Jun. 2002, pp. 447-456.

Derveaux et al., "Layer-by-Layer Coated Digitally Encoded Microcarriers for Quantification of Proteins in Serum and Plasma", Analytical Chemistry, Dec. 4, 2007, pp. 85-94.

International Search Report and Written Opinion received for PCT Patent Application No. PCT/IB2016/000937, dated Oct. 27, 2016, 7 pages.

Chung et al., Unpublished U.S. Appl. No. 15/460,657, filed Mar. 16, 2017, titled "Methods and Systems for Image Differentiated Multiplex Assays".

* cited by examiner

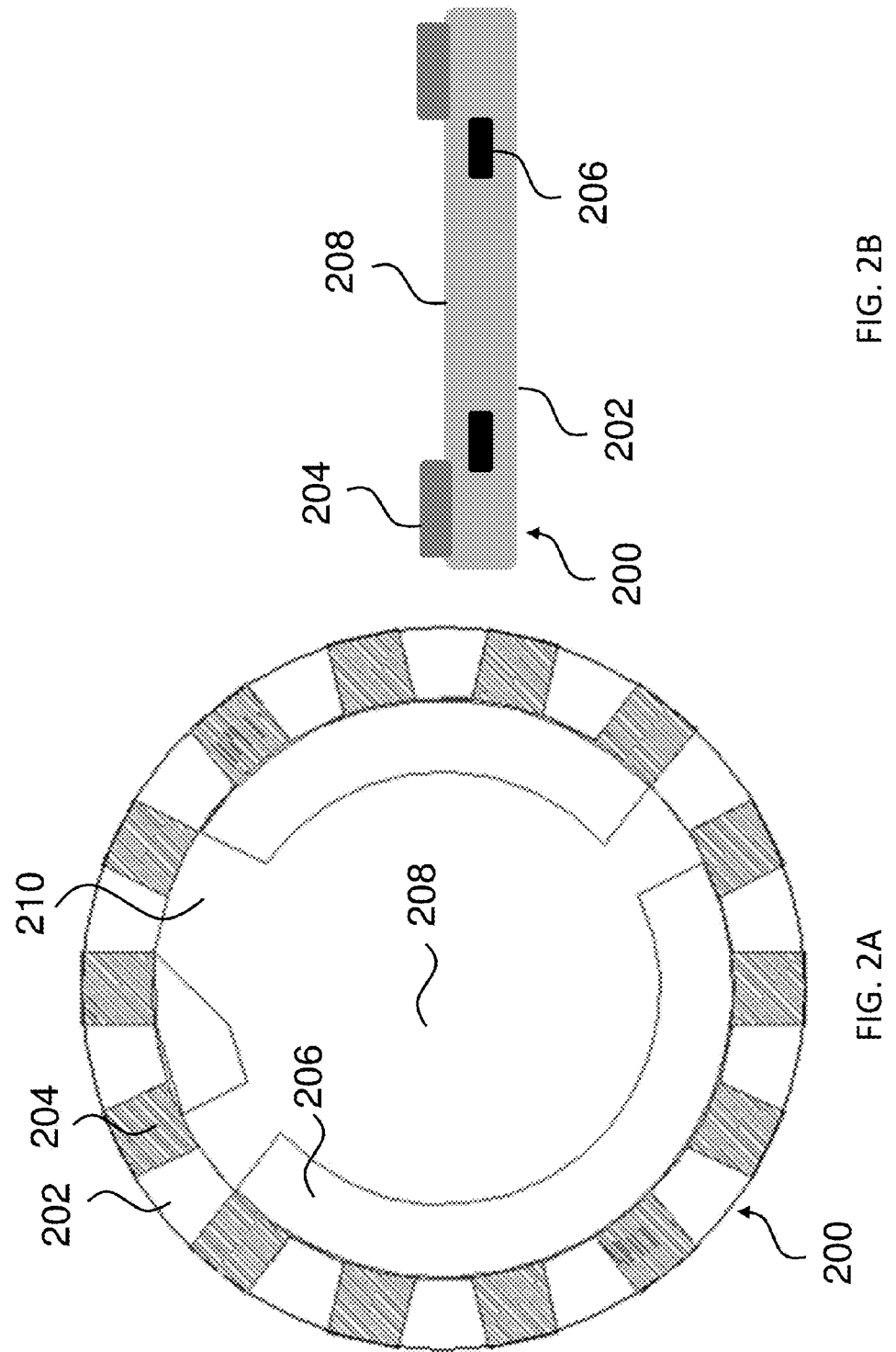

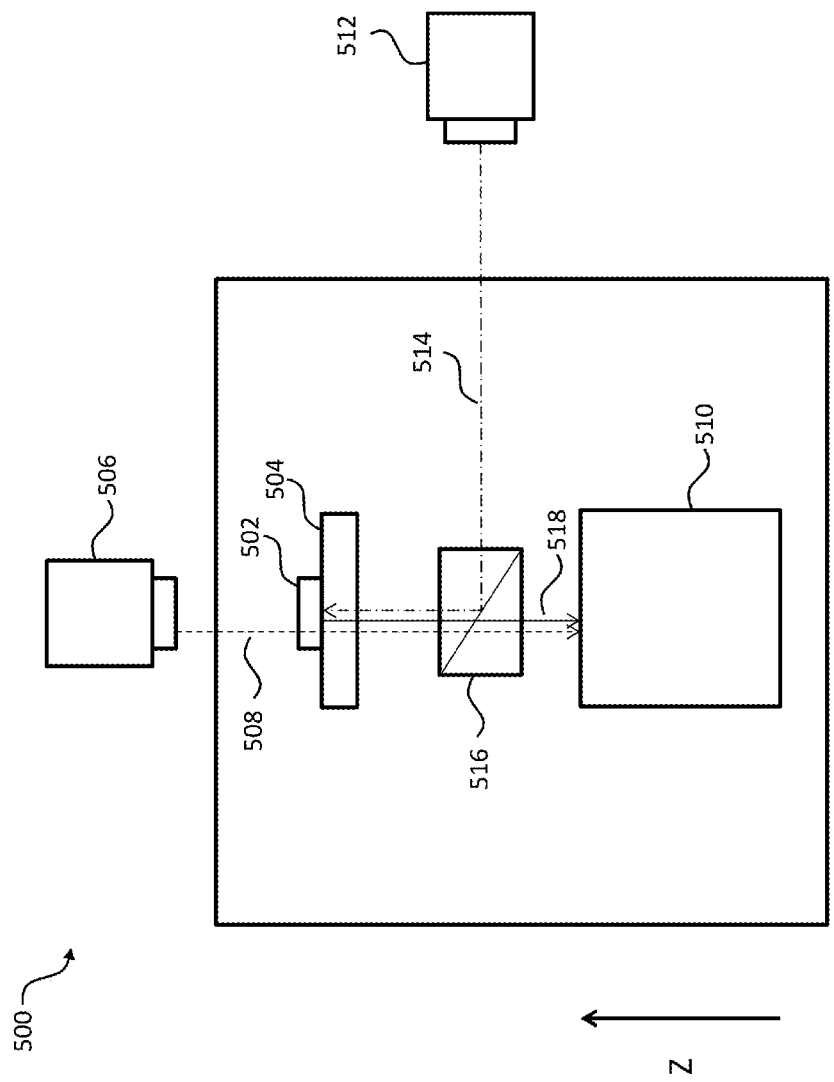

METHODS AND SYSTEMS FOR SELECTION OF DETECTION AREA

CROSS REFERENCE TO RELATED APPLICATIONS

This application claims the priority benefit of U.S. Provisional Application Ser. No. 62/258,388, filed Nov. 20, 2015, which is incorporated herein by reference in its entirety.

FIELD

Provided herein are methods and systems for selecting a detection area for a well comprising a plurality of encoded microcarriers. The methods and systems involve, e.g., determining the distance between the position of an encoded microcarrier and the well center, wherein the detection area includes only those microcarriers whose distance from the center does not exceed a threshold distance.

BACKGROUND

Immunological and molecular diagnostic assays play a critical role both in the research and clinical fields. Often it is necessary to perform assays for a panel of multiple targets to gain a meaningful or bird's-eye view of results to facilitate research or clinical decision-making. This is particularly true in the era of genomics and proteomics, where an abundance of genetic markers and/or biomarkers are thought to influence or be predictive of particular disease states. In theory, assays of multiple targets can be accomplished by testing each target separately in parallel or sequentially in different reaction vessels (i.e., multiple singleplexing). However, not only are assays adopting a singleplexing strategy often cumbersome, but they also typically required large sample volumes, especially when the targets to be analyzed are large in number.

A multiplex assay simultaneously measures multiple analytes (two or more) in a single assay. Multiplex assays are commonly used in high-throughput screening settings, where many specimens can be analyzed at once. It is the ability to assay many analytes simultaneously and many specimens in parallel that is the hallmark of multiplex assays and is the reason that such assays have become a powerful tool in fields ranging from drug discovery to functional genomics to clinical diagnostics. In contrast to singleplexing, by combining all targets in the same reaction vessel, the assay is much less cumbersome and much easier to perform, since only one reaction vessel is handled per sample. The required test samples can thus be dramatically reduced in volume, which is especially important when samples (e.g., tumor tissues, cerebral spinal fluid, or bone marrow) are difficult and/or invasive to retrieve in large quantities. Equally important is the fact that the reagent cost can be decreased and assay throughput increased drastically.

Many assays of complex macromolecule samples are composed of two steps. In the first step, agents capable of specifically capturing the target macromolecules are attached to a solid phase surface. These immobilized molecules may be used to capture the target macromolecules from a complex sample by various means, such as hybridization (e.g., in DNA, RNA based assays) or antigen-antibody interactions (in immunoassays). In the second step, detection molecules are incubated with and bind to the complex of capture molecule and the target, emitting signals such as fluorescence or other electromagnetic signals. The amount of the target is then quantified by the intensity of those signals.

Multiplex assays may be carried out by utilizing multiple capture agents, each specific for a different target macromolecule. In chip-based array multiplex assays, each type of capture agent is attached to a pre-defined position on the chip. The amount of multiplex targets in a complex sample is determined by measuring the signal of the detection molecule at each position corresponding to a type of capture agent. In suspension array multiplex assays, microparticles or microcarriers are suspended in the assay solution. These microparticles or microcarriers contain an identification element, which may be embedded, printed, or otherwise generated by one or more elements of the microparticle/microcarrier. Each type of capture agent is immobilized to particles with the same ID, and the signals emitted from the detection molecules on the surface of the particles with a particular ID reflect the amount of the corresponding target.

Accurate measurements are highly desirable for analyte detection, e.g., multiplex assays. Microcarrier-based analyte detection assays are often performed using microwell assay plates. Such plates allow for high-throughput analysis of multiple samples and/or analytes. However, these plates can also introduce systematic errors into the detection process. For example, in light-based detection assays (e.g., fluorescence or luminescence), the microwell plates themselves may interfere with light detection. The well edges may perturb light measurements of nearby microcarriers, for example by reflecting light and/or providing an uneven surface (e.g., a curved well edge may push nearby microcarriers out of the same focal plane as those microcarriers farther away from the edge, leading to potential distortion of light-based measurements).

Therefore, a need exists for methods, systems, devices, and computer-readable storage media that reduce these sources of systematic error. Such methods, systems, devices, and computer-readable storage media not only allow a user to remove these sources of error, but they also allow the user to apply the same error correction across multiple samples. This standardizes the detection of each sample to a uniform set of parameters for greater reproducibility and consistency.

All publications, patents, and patent applications cited herein are hereby incorporated by reference in their entirety for all purposes.

BRIEF SUMMARY

To meet this need, provided herein, inter alia, are methods and systems for selecting a detection area for a well comprising a plurality of encoded microcarriers. These methods and systems may be used, inter alia, to reduce variation in microcarrier-based multiplexed assays, e.g., in which each microcarrier includes a capture agent for capturing a specific analyte and a code for identification. Devices and computer-readable storage media related thereto are further provided.

Prior to the present disclosure, it was difficult to adapt existing plate readers and their software to imaging (e.g., by fluorescence detection) a plurality microcarriers in an assay plate well. It is advantageous to include many microcarriers in a single well in order to increase sample size and therefore assay accuracy and/or to increase the number of different analytes that can be detected in a single multiplex assay. However, an increased number of microcarriers means that more microcarriers are likely to be situated near the walls of the assay plate well, leading to perturbation of light measurements. As shown in the Example below, detecting the entire assay plate well (including microcarriers near to the assay plate walls) can lead to systematic errors and large variance in light measurements. In order to solve this problem, the user can manually mark detection areas for individual microcarriers not situated near the assay plate walls. However, this introduces a time constraint that is impractical for implementation of assays with large numbers of wells and/or microcarriers in each well. The methods, systems, devices, and computer-readable storage media of the present disclosure improve upon existing technology by implementing a specific set of rules in a combination that allows the user to solve this problem of accurately measuring signal (e.g., from fluorescence imaging data) from a well containing a plurality of microcarriers. These specific rules allow the user to balance sample size with sample variance in order to provide accurate measurements, thereby solving a specific problem in imaging biological assay results, e.g., using an encoded microcarrier with one or more capture agents, analytes, and detection reagents.

Accordingly, in one aspect, provided herein are methods for selecting a detection area for a well comprising a plurality of encoded microcarriers, comprising: obtaining one or more images of the well comprising the plurality of encoded microcarriers; calculating a center of the well, according to a two-dimensional coordinate system, based on the one or more images; assigning a position, according to the two-dimensional coordinate system, of a first encoded microcarrier from the plurality of encoded microcarriers based on the one or more images; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area. In another aspect, provided herein are methods for selecting a detection area for a well comprising a plurality of encoded microcarriers at an electronic device comprising one or more processors, the methods comprising: obtaining data representing one or more images of the well comprising the plurality of encoded microcarriers; calculating a center of the well, according to a two-dimensional coordinate system, based on the obtained data; assigning a position, according to the two-dimensional coordinate system, of a first encoded microcarrier from the plurality of encoded microcarriers based on the obtained data; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area. In another aspect, provided herein are methods for selecting a detection area for a well comprising a plurality of encoded microcarriers at an electronic device comprising one or more processors, an objective, a light source, a camera, and an assay plate positioned on a detection stage, the assay plate comprising the well comprising the plurality of encoded microcarriers, the methods comprising: obtaining data representing one or more images of the well comprising the plurality of encoded microcarriers, wherein the data representing the one or more images of the well are obtained by the camera using the objective and the light source; calculating a center of the well, according to a two-dimensional coordinate system, based on the obtained data; assigning a position, according to the two-dimensional coordinate system, of a first encoded microcarrier from the plurality of encoded microcarriers based on the obtained data; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area.

In some embodiments, the methods further comprise decoding a code of the first encoded microcarrier. In some embodiments, in accordance with the determination that the distance between the position of the first encoded microcarrier and the center of the well does not exceed the threshold distance, the methods further comprise: detecting an amount of an analyte bound to the first encoded microcarrier in the detection area. In some embodiments, detecting the amount of the analyte bound to the first encoded microcarrier comprises detecting an amount of fluorescence in the position of the first encoded microcarrier. In some embodiments, detecting the amount of the analyte bound to the first encoded microcarrier comprises detecting an amount of luminescence in the position of the first encoded microcarrier. In some embodiments, the first encoded microcarrier comprises: (a) a substantially transparent polymer layer having a first surface and a second surface, the first and the second surfaces being parallel to each other; (b) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code; (c) a capture agent for capturing an analyte, wherein the capture agent is coupled to at least one of the first surface and the second surface of the substantially transparent polymer layer in at least the center portion of the substantially transparent polymer layer; (d) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (e) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the plurality of encoded microcarriers comprises: (i) a first subset of one or more encoded microcarriers, wherein each microcarrier of the first subset comprises a first code and a first capture agent that specifically recognizes a first analyte; and (ii) a second subset of one or more encoded microcarriers, wherein each microcarrier of the second subset comprises a second code and a second capture agent, and wherein the second code is different from the first code. In some embodiments, the second capture agent specifically recognizes a second analyte that is different from the first analyte. In some embodiments, the second capture agent specifically recognizes the first analyte. In some embodiments, the methods further comprise receiving data representing a user selection of the threshold distance. In some embodiments, the one or more images of the well comprises a plurality of images of the well, the plurality of images of the well comprises at least one well image that does not comprise the calculated center of the well, the first microcarrier is represented in the at least one well image that does not comprise the calculated center of the well, and assigning the position of the first microcarrier comprises transforming an image coordinate of the first microcarrier to a two-dimensional well coordinate of the first microcarrier according to the two-dimensional coordinate system. In some embodiments, calculating the center of the well further comprises transforming the center of the well according to the two-dimensional coordinate system to a center of the well according to a pixel-based system; assigning the position of the first encoded microcarrier further comprises transforming the position of the first encoded microcarrier according to the two-dimensional coordinate system to a position of the first encoded microcarrier according to the pixel-based system; and determining whether the distance between the position of the first encoded microcarrier and the center of the well exceeds a threshold distance further comprises comparing the threshold distance with the distance between the position of the first encoded microcarrier and the center of the well according to the pixel-based system. In some embodiments, the methods further comprise generating a depiction of at least a portion of the detection area, the depiction depicting one or more encoded microcarriers included in said detection area. In some embodiments, the depiction further depicts a representation of one or more encoded microcarriers excluded from the detection area. In some embodiments, the well is a circular well. In some embodiments, the well further comprises a biological sample comprising the plurality of encoded microcarriers.

In another aspect, provided herein are systems comprising an objective, a camera, a light source, a detection stage, one or more processors, a memory, and one or more programs stored in the memory, wherein the one or more programs are configured to be executed by the one or more processors, and wherein the one or more programs include instructions for: obtaining data representing one or more images of a well of an assay plate positioned on the detection stage, wherein the well comprises a plurality of encoded microcarriers, and wherein the data representing the one or more images of the well are obtained by the camera using the objective and the light source; calculating a center of the well, according to a two-dimensional coordinate system, based on the obtained data; assigning a position, according to the two-dimensional coordinate system, of a first encoded microcarrier from the plurality of encoded microcarriers based on the obtained data; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from a detection area; and in accordance with a determination that the distance between the position of the first encoded microcarrier and the center of the well does not exceed the threshold distance: including the first encoded microcarrier in the detection area, thereby selecting the detection area.

In some embodiments, the one or more programs further include instructions for decoding a code of the first encoded microcarrier. In some embodiments, the one or more programs further include instructions for: in accordance with the determination that the distance between the position of the first encoded microcarrier and the center of the well does not exceed the threshold distance, detecting an amount of an analyte bound to the first encoded microcarrier in the detection area. In some embodiments, detecting the amount of the analyte bound to the first encoded microcarrier comprises detecting an amount of fluorescence in the position of the first encoded microcarrier. In some embodiments, detecting the amount of the analyte bound to the first encoded microcarrier comprises detecting an amount of luminescence in the position of the first encoded microcarrier. In some embodiments, the first encoded microcarrier comprises: (a) a substantially transparent polymer layer having a first surface and a second surface, the first and the second surfaces being parallel to each other; (b) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code; (c) a capture agent for capturing an analyte, wherein the capture agent is coupled to at least one of the first surface and the second surface of the substantially transparent polymer layer in at least the center portion of the substantially transparent polymer layer; (d) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (e) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the plurality of encoded microcarriers comprises: (i) a first subset of one or more encoded microcarriers, wherein each microcarrier of the first subset comprises a first code and a first capture agent that specifically recognizes a first analyte; and (ii) a second subset of one or more encoded microcarriers, wherein each microcarrier of the second subset comprises a second code and a second capture agent, wherein the second code is different from the first code. In some embodiments, the second capture agent specifically recognizes a second analyte that is different from the first analyte. In some embodiments, the second capture agent specifically recognizes the first analyte. In some embodiments, the one or more programs further include instructions for: receiving data representing a user selection of the threshold distance. In some embodiments, the one or more images of the well comprises a plurality of images of the well, the plurality of images of the well comprises at least one well image that does not comprise the calculated center of the well, the first microcarrier is represented in the at least one well image that does not comprise the calculated center of the well, and assigning the position of the first microcarrier comprises transforming an image coordinate of the first microcarrier to a two-dimensional well coordinate of the first microcarrier according to the two-dimensional coordinate system. In some embodiments, calculating the center of the well further comprises transforming the center of the well according to the two-dimensional coordinate system to a center of the well according to a pixel-based system; assigning the position of the first encoded microcarrier further comprises transforming the position of the first encoded microcarrier according to the two-dimensional coordinate system to a position of the first encoded microcarrier according to the pixel-based system; and determining whether the distance between the position of the first encoded microcarrier and the center of the well exceeds a threshold distance further comprises comparing the threshold distance with the distance between the position of the first encoded microcarrier and the center of the well according to the pixel-based system. In some embodiments, the one or more programs further include instructions for: generating a depiction of at least a portion of the detection area, the depiction depicting one or more encoded microcarriers included in said detection area. In some embodiments, the depiction further depicts a representation of one or more encoded microcarriers excluded from the detection area. In some embodiments, the well is a circular well. In some embodiments, the well further comprises a biological sample comprising the plurality of encoded microcarriers.

In another aspect, provided herein are non-transitory computer-readable storage media comprising one or more programs for execution by one or more processors of a device with an objective, a camera, a light source, and a detection stage, the one or more programs including instructions which, when executed by the one or more processors, cause the device to: obtain data representing one or more images of a well of an assay plate positioned on the detection stage, wherein the well comprises a plurality of encoded microcarriers, and wherein the data representing the one or more images of the well are obtained by the camera using the objective and the light source; calculate a center of the well, according to a two-dimensional coordinate system, based on the obtained data; assign a position, according to the two-dimensional coordinate system, of a first encoded microcarrier from the plurality of encoded microcarriers based on the obtained data; determine whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude the first encoded microcarrier from a detection area; and in accordance with a determination that the distance between the position of the first encoded microcarrier and the center of the well does not exceed the threshold distance: include the first encoded microcarrier in the detection area, thereby selecting the detection area. In another aspect, provided herein are non-transitory computer-readable storage media comprising one or more programs for execution by one or more processors of an electronic device, the one or more programs including instructions which, when executed by the one or more processors, cause the electronic device to: obtain data representing one or more images of a well of an assay plate positioned on the detection stage, wherein the well comprises a plurality of encoded microcarriers; calculate a center of the well, according to a two-dimensional coordinate system, based on the obtained data; assign a position, according to the two-dimensional coordinate system, of a first encoded microcarrier from the plurality of encoded microcarriers based on the obtained data; determine whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude the first encoded microcarrier from a detection area; and in accordance with a determination that the distance between the position of the first encoded microcarrier and the center of the well does not exceed the threshold distance: include the first encoded microcarrier in the detection area, thereby selecting the detection area. In another aspect, provided herein are non-transitory computer-readable storage media comprising one or more programs for execution by one or more processors of an electronic device with an objective, a camera, a light source, and a detection stage, the one or more programs including instructions which, when executed by the one or more processors, cause the electronic device to perform the method of any one of the above embodiments. In another aspect, provided herein are non-transitory computer-readable storage media comprising one or more programs for execution by one or more processors of an electronic device, the one or more programs including instructions which, when executed by the one or more processors, cause the electronic device to perform the method of any one of the above embodiments.

In another aspect, provided herein are electronic imaging devices comprising an objective, a camera, a light source, a detection stage, and a processing unit, the processing unit coupled to the objective, the camera, the light source, and the detection stage, the processing unit configured to: obtain, using the objective, the light source, and the camera, data representing one or more images of a well of an assay plate positioned on the detection stage, wherein the well comprises a plurality of encoded microcarriers; calculate a center of the well, according to a two-dimensional coordinate system, based on the obtained data; assign a position, according to the two-dimensional coordinate system, of a first encoded microcarrier from the plurality of encoded microcarriers based on the obtained data; determine whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude the first encoded microcarrier from a detection area; and in accordance with a determination that the distance between the position of the first encoded microcarrier and the center of the well does not exceed the threshold distance: include the first encoded microcarrier in the detection area, thereby selecting the detection area.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIGS. 2A & 2B show two views of an exemplary microcarrier.

FIGS. 3A-3C show an exemplary method for calculating a well center based on multiple images of the well perimeter.

FIGS. 5A & 5B show functional block diagrams for detection systems/devices in accordance with some embodiments. The z-axis is labeled in FIG. 5A.

DETAILED DESCRIPTION

Figure 1:
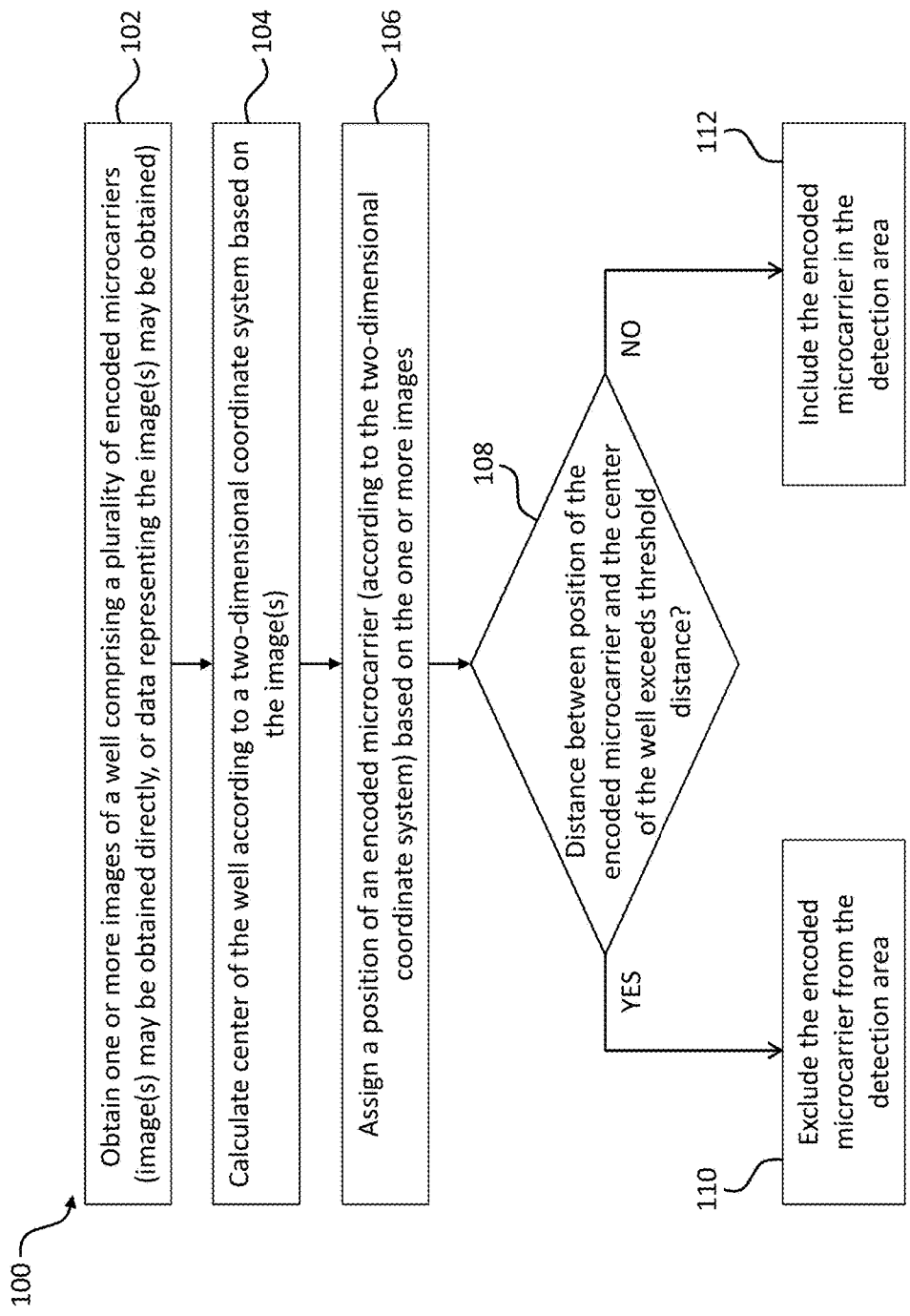
FIG. 1 is a flow diagram illustrating a method for selection of detection area in accordance with some embodiments.

In one aspect, provided herein are methods for selecting a detection area for a well comprising a plurality of encoded microcarriers. In some embodiments, the methods comprise obtaining one or more images of the well comprising the plurality of encoded microcarriers; calculating a center of the well, according to a two-dimensional coordinate system, based on the one or more images; assigning a position, according to the two-dimensional coordinate system, of a first encoded microcarrier from the plurality of encoded microcarriers based on the one or more images; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area. In some embodiments, the methods are at an electronic device comprising one or more processors and comprise obtaining (e.g., using the one or more processors) one or more images of the well comprising the plurality of encoded microcarriers; calculating (e.g., using the one or more processors) a center of the well, according to a two-dimensional coordinate system, based on the one or more images; assigning (e.g., using the one or more processors) a position, according to the two-dimensional coordinate system, of a first encoded microcarrier from the plurality of encoded microcarriers based on the one or more images; determining (e.g., using the one or more processors) whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area. In some embodiments, the methods are at an electronic device comprising one or more processors, an objective, a light source, a camera, and an assay plate positioned on a detection stage, the assay plate comprising the well comprising the plurality of encoded microcarriers, and comprise obtaining (e.g., using the one or more processors) data representing one or more images of the well comprising the plurality of encoded microcarriers, wherein the data representing the one or more images of the well are obtained by the camera using the objective and the light source; calculating (e.g., using the one or more processors) a center of the well, according to a two-dimensional coordinate system, based on the obtained data; assigning (e.g., using the one or more processors) a position, according to the two-dimensional coordinate system, of a first encoded microcarrier from the plurality of encoded microcarriers based on the obtained data; determining (e.g., using the one or more processors) whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area.

In another aspect, provided herein are systems comprising an objective, a camera, a light source, a detection stage, one or more processors, a memory, and one or more programs stored in the memory, wherein the one or more programs are configured to be executed by the one or more processors, and wherein the one or more programs include instructions for: obtaining data representing one or more images of a well of an assay plate positioned on the detection stage, wherein the well comprises a plurality of encoded microcarriers, and wherein the data representing the one or more images of the well are obtained by the camera using the objective and the light source; calculating a center of the well, according to a two-dimensional coordinate system, based on the obtained data; assigning a position, according to the two-dimensional coordinate system, of a first encoded microcarrier from the plurality of encoded microcarriers based on the obtained data; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from a detection area; and in accordance with a determination that the distance between the position of the first encoded microcarrier and the center of the well does not exceed the threshold distance: including the first encoded microcarrier in the detection area, thereby selecting the detection area.

In another aspect, provided herein are non-transitory computer-readable storage media comprising one or more programs for execution by one or more processors of a device with an objective, a camera, a light source, and a detection stage, the one or more programs including instructions which, when executed by the one or more processors, cause the device to: obtain data representing one or more images of a well of an assay plate positioned on the detection stage, wherein the well comprises a plurality of encoded microcarriers, and wherein the data representing the one or more images of the well are obtained by the camera using the objective and the light source; calculate a center of the well, according to a two-dimensional coordinate system, based on the obtained data; assign a position, according to the two-dimensional coordinate system, of a first encoded microcarrier from the plurality of encoded microcarriers based on the obtained data; determine whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude the first encoded microcarrier from a detection area; and in accordance with a determination that the distance between the position of the first encoded microcarrier and the center of the well does not exceed the threshold distance: include the first encoded microcarrier in the detection area, thereby selecting the detection area.

In another aspect, provided herein are electronic imaging devices comprising an objective, a camera, a light source, a detection stage, and a processing unit, the processing unit coupled to the objective, the camera, the light source, and the detection stage, the processing unit configured to: obtain, using the objective, the light source, and the camera, data representing one or more images of a well of an assay plate positioned on the detection stage, wherein the well comprises a plurality of encoded microcarriers; calculate a center of the well, according to a two-dimensional coordinate system, based on the obtained data; assign a position, according to the two-dimensional coordinate system, of a first encoded microcarrier from the plurality of encoded microcarriers based on the obtained data; determine whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude the first encoded microcarrier from a detection area; and in accordance with a determination that the distance between the position of the first encoded microcarrier and the center of the well does not exceed the threshold distance: include the first encoded microcarrier in the detection area, thereby selecting the detection area.

I. General Techniques

The practice of the techniques described herein will employ, unless otherwise indicated, conventional techniques in polymer technology, microfabrication, micro-electro-mechanical systems (MEMS) fabrication, photolithography, microfluidics, organic chemistry, biochemistry, oligonucleotide synthesis and modification, bioconjugate chemistry, nucleic acid hybridization, molecular biology, microbiology, genetics, recombinant DNA, and related fields as are within the skill of the art. The techniques are described in the references cited herein and are fully explained in the literature.

For molecular biology and recombinant DNA techniques, see, for example, (Maniatis, T. et al. (1982), *Molecular Cloning: A Laboratory Manual*, Cold Spring Harbor; Ausubel, F. M. (1987), *Current Protocols in Molecular Biology*, Greene Pub. Associates and Wiley-Interscience; Ausubel, F. M. (1989), *Short Protocols in Molecular Biology: A Compendium of Methods from Current Protocols in Molecular Biology*, Greene Pub. Associates and Wiley-Interscience; Sambrook, J. et al. (1989), *Molecular Cloning: A Laboratory Manual*, Cold Spring Harbor; Innis, M. A. (1990), *PCR Protocols: A Guide to Methods and Applications*, Academic Press; Ausubel, F. M. (1992), *Short Protocols in Molecular Biology: A Compendium of Methods from Current Protocols in Molecular Biology*, Greene Pub. Associates; Ausubel, F. M. (1995), *Short Protocols in Molecular Biology: A Compendium of Methods from Current Protocols in Molecular Biology*, Greene Pub. Associates; Innis, M. A. et al. (1995), *PCR Strategies, Academic Press*; Ausubel, F. M. (1999), *Short Protocols in Molecular Biology: A Compendium of Methods from Current Protocols in Molecular Biology*, Wiley, and annual updates.

For DNA synthesis techniques and nucleic acids chemistry, see for example, Gait, M. J. (1990), *Oligonucleotide Synthesis: A Practical Approach*, IRL Press; Eckstein, F. (1991), *Oligonucleotides and Analogues: A Practical Approach*, IRL Press; Adams, R. L. et al. (1992), *The Biochemistry of the Nucleic Acids*, Chapman & Hall; Shabarova, Z. et al. (1994), *Advanced Organic Chemistry of Nucleic Acids*, Weinheim; Blackburn, G. M. et al. (1996), *Nucleic Acids in Chemistry and Biology*, Oxford University Press; Hermanson, G. T. (1996), *Bioconjugate Techniques*, Academic Press).

For microfabrication, see for example, (Campbell, S. A. (1996), *The Science and Engineering of Microelectronic Fabrication*, Oxford University Press; Zaut, P. V. (1996), *Microarray Fabrication: a Practical Guide to Semiconductor Processing*, Semiconductor Services; Madou, M. J. (1997), *Fundamentals of Microfabrication*, CRC Press; Rai-Choudhury, P. (1997). Handbook of Microlithography, Micromachining, & Microfabrication: Microlithography).

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

The term "microcarrier" as used herein may refer to a physical substrate onto which a capture agent may be coupled. A microcarrier of the present disclosure may take any suitable geometric form or shape. In some embodiments, the microcarrier may be disc-shaped. Typically the form or shape of a microcarrier will include at least one dimension on the order of $10^{-4}$ to $10^{-7}$ m (hence the prefix "micro").

The term "polymer" as used herein may refer to any macromolecular structure comprising repeated monomers. A polymer may be natural (e.g., found in nature) or synthetic (e.g., man-made, such as a polymer composed of non-natural monomer(s) and/or polymerized in a configuration or combination not found in nature).

The terms "substantially transparent" and "substantially non-transparent" as used herein may refer to the ability of light (e.g., of a particular wavelength, such as infrared, visible, UV, and so forth) to pass through a substrate, such as a polymer layer. A substantially transparent polymer may refer to one that is transparent, translucent, and/or pervious to light, whereas a substantially non-transparent polymer may refer to one that reflects and/or absorbs light. It is to be appreciated that whether a material is substantially transparent or substantially non-transparent may depend upon the wavelength and/or intensity of light illuminating the material, as well as the means detecting the light traveling through the material (or a decrease or absence thereof). In some embodiments, a substantially non-transparent material causes a perceptible decrease in transmitted light as compared to the surrounding material or image field, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy). In some embodiments, a substantially transparent material allows a perceptible amount of transmitted light to pass through the material, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy).

The term "analog code" as used herein may refer to any code in which the encoded information is represented in a non-quantized and/or non-discrete manner, e.g., as opposed to a digital code. For example, a digital code is sampled at discrete positions for a limited set of values (e.g., 0/1 type values), whereas an analog code may be sampled at a greater range of positions (or as a continuous whole) and/or may contain a wider set of values (e.g., shapes). In some embodiments, an analog code may be read or decoded using one or more analog shape recognition techniques.

The term "capture agent" as used herein is a broad term and is used in its ordinary sense to refer to any compound or substance capable of specifically recognizing an analyte of interest. In some embodiments, specific recognition may refer to specific binding. Non-limiting examples of capture agents include, for example, a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

"Analyte," as used herein, is a broad term and is used in its ordinary sense as a substance the presence, absence, or quantity of which is to be determined, including, without limitation, to refer to a substance or chemical constituent in a sample such as a biological sample or cell or population of cells that can be analyzed. An analyte can be a substance for which a naturally occurring binding member exists, or for which a binding member can be prepared. Non-limiting examples of analytes include, for example, antibodies, antibody fragments, antigens, polynucleotides (such as a DNA molecule, DNA-analog-molecule, RNA-molecule, or RNA-analog-molecule), polypeptides, proteins, enzymes, lipids, phospholipids, carbohydrate moieties, polysaccharides, small molecules, organelles, hormones, cytokines, growth factors, steroids, vitamins, toxins, drugs, and metabolites of the above substances, as well as cells, bacteria, viruses, fungi, algae, fungal spores and the like.

The term "antibody" is used in the broadest sense and includes monoclonal antibodies (including full length antibodies which have an immunoglobulin Fc region), polyclonal antibodies, multispecific antibodies (e.g., bispecific antibodies, diabodies, and single-chain molecules), as well as antibody fragments (e.g., Fab, $F(ab')_2$, and Fv).

As used herein, "sample" refers to a composition containing a material, such as a molecule, to be detected. In one embodiment, the sample is a "biological sample" (i.e., any material obtained from a living source (e.g. human, animal, plant, bacteria, fungi, protist, virus)). The biological sample can be in any form, including solid materials (e.g. tissue, cell pellets and biopsies) and biological fluids (e.g. urine, blood, saliva, lymph, tears, sweat, prostatic fluid, seminal fluid, semen, bile, mucus, amniotic fluid and mouth wash (containing buccal cells)). Solid materials typically are mixed with a fluid. Sample can also refer to an environmental sample such as water, air, soil, or any other environmental source.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

III. Methods for Selection of Detection Area

Provided herein are methods for selecting a detection area for a well comprising a plurality of encoded microcarriers. These methods may be used in any of the systems, devices, and computer-readable storage media described herein. The methods, devices, systems, and computer-readable storage media described herein may find use, inter alia, in in multiplex assays for analyte detection.

In some embodiments, the methods of the present disclosure comprise obtaining one or more images of the well comprising the plurality of encoded microcarriers; calculating a center of the well, according to a two-dimensional coordinate system, based on the one or more images; assigning a position, according to the two-dimensional coordinate system, of a first encoded microcarrier from the plurality of encoded microcarriers based on the one or more images; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area. In other embodiments, the methods of the present disclosure comprise obtaining data representing one or more images of the well comprising the plurality of encoded microcarriers; calculating a center of the well, according to a two-dimensional coordinate system, based on the obtained data; assigning a position, according to the two-dimensional coordinate system, of a first encoded microcarrier from the plurality of encoded microcarriers based on the obtained data; determining whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: excluding the first encoded microcarrier from the detection area; and in accordance with a determination that the distance between the position of the first encoded microcarrier and the center of the well does not exceed the threshold distance: including the first encoded microcarrier in the detection area, thereby selecting the detection area.

In accordance with some embodiments, a flow diagram illustrating exemplary process 100 for selecting detection area is provided in FIG. 1. In some embodiments, process 100 may be performed using a system or device of the present disclosure, including without limitation the exemplary detection systems/devices illustrated in FIGS. 5A and 5B. In some embodiments, process 100 may be performed to select a detection area for one or more images in a well comprising a plurality of encoded microcarriers of the present disclosure. Different embodiments of encoded microcarriers are described in greater detail infra in section IV. One non-limiting example of an encoded microcarrier is illustrated in FIGS. 2A-2D and further described infra.

At block 102, one or more images of a well comprising a plurality of encoded microcarriers are obtained. Alternatively, at block 102, data representing one or more images of a well comprising a plurality of encoded microcarriers are obtained. At block 104, a center of the well is calculated, according to a two-dimensional coordinate system, based on the one or more images (or data representing them). At block 106, a position of a first microcarrier of the plurality is assigned, according to the two-dimensional coordinate system (e.g., the same system used at block 104), based on the one or more images (or data representing them). At block 108, a determination is made as to whether the distance between the position of the first microcarrier and the calculated well center exceeds a threshold distance. At block 110, in accordance with a determination that the distance between the position of the first microcarrier and the calculated well center exceeds the threshold distance, the first microcarrier is excluded from the detection area. At block 112, in accordance with a determination that the distance between the position of the first microcarrier and the calculated well center does not exceed the threshold distance, the first microcarrier is included in the detection area. Thus, the detection area is selected.

By assigning each microcarrier a position relative to the center of an assay plate well according to a same two-dimensional coordinate system, a threshold distance can be set in order to balance the conflicting demands of increasing sample size and exclusion of detection events that are potentially perturbed by proximity to the wall of an assay plate well. The implementation of this combination of steps improves existing fluorescence imaging devices (e.g., plate readers) and software by allowing the user to balance these demands and obtain accurate measurements of a large number of individual microcarriers in the well of an assay plate. Further, this specific implementation overcomes problems in adapting plate reader technology to obtain accurate optical measurements of detection reagents interacting with capture agents coupled to encoded microcarriers and analytes of interest.

Some operations in process 100 may be combined, the order of some operations may be changed, and some operations may be omitted. In addition, one of skill in the art will appreciate that the order of operations depicted in FIG. 1 is exemplary and does not indicate that the depicted order is the only order in which the operations may be performed. One of ordinary skill in the art would recognize various ways to reorder the operations described herein, as well as excluding certain operations; for brevity, these permutations are not repeated herein.

In some embodiments, one or more images of a well comprising a plurality of encoded microcarriers are obtained (e.g., as shown in block 102). In some embodiments, the image(s) of the well are obtained using a system or device of the present disclosure (see, e.g., block 602 in FIG. 6). In some embodiments, a single image of the well is obtained. In other embodiments, more than one image of the well is obtained (see, e.g., FIGS. 3A and 7, which illustrate a single well reconstructed from 21 images). In some embodiments, the images are partially overlapping. This may allow for greater chances that all microcarriers in the well are captured in at least one image. In other embodiments, the images are non-overlapping.

In some embodiments, the one or more images comprise a bright-field image. In some embodiments, the one or more images comprise a fluorescence image. In certain embodiments, corresponding bright-field and fluorescence images are obtained for a single field (e.g., a set of 21 bright-field images is obtained, along with 21 fluorescence images that each correspond to one of the bright-field images). For example, one or more processors of the present disclosure may be used to retrieve multiple sub-images, obtained via image scanning, and combine the sub-images into a reconstructed well image (see, e.g., FIGS. 3A and 7). In some embodiments, the one or more processors are used to identify the code of each microcarrier and determine an associated fluorescence reading for the microcarrier, as described herein. That is, the barcode information and the fluorescence information associated with respective beads in the well image can be identified and utilized for further analysis. Advantageously, this makes it possible to image a well of encoded microcarriers for multiple parameters including detection of an analyte of interest and decoding the microcarrier code for identification of the corresponding capture agent (and thus, analyte), which is essential for the ability to use this technology for multiplex assays. In some embodiments, one or more bright-field and/or fluorescence images may be stored for analysis/retrieval in a memory of the present disclosure. In some embodiments, the one or more images are obtained by a camera, e.g., coupled to a light source and objective of the present disclosure.

In some embodiments, data representing one or more images of a well comprising a plurality of encoded microcarriers are obtained (e.g., as shown in block 102). It will be appreciated by one of skill in the art that the methods described herein may be applied to one or more images obtained by a device or system of the present disclosure, as well as one or more images obtained by a separate device. For example, a set of existing images may be analyzed using the methods, devices, systems, and/or computer-readable storage media of the present disclosure. In some embodiments, the data representing one or more images of the well are obtained by one or more processors of the present disclosure.

In some embodiments, a center of a well is calculated according to a two-dimensional coordinate system, based on the one or more images, or data representative thereof (e.g., as shown in block 104). Examples of two-dimensional coordinate systems include, without limitation, a Cartesian coordinate system.

In some embodiments, the center of the well is calculated based on one image of the well. Methods for determining the center of a geometric shape suitable for calculation of a corresponding well are well known in the art. In certain embodiments, the well is a circular well.

Figure 3A:
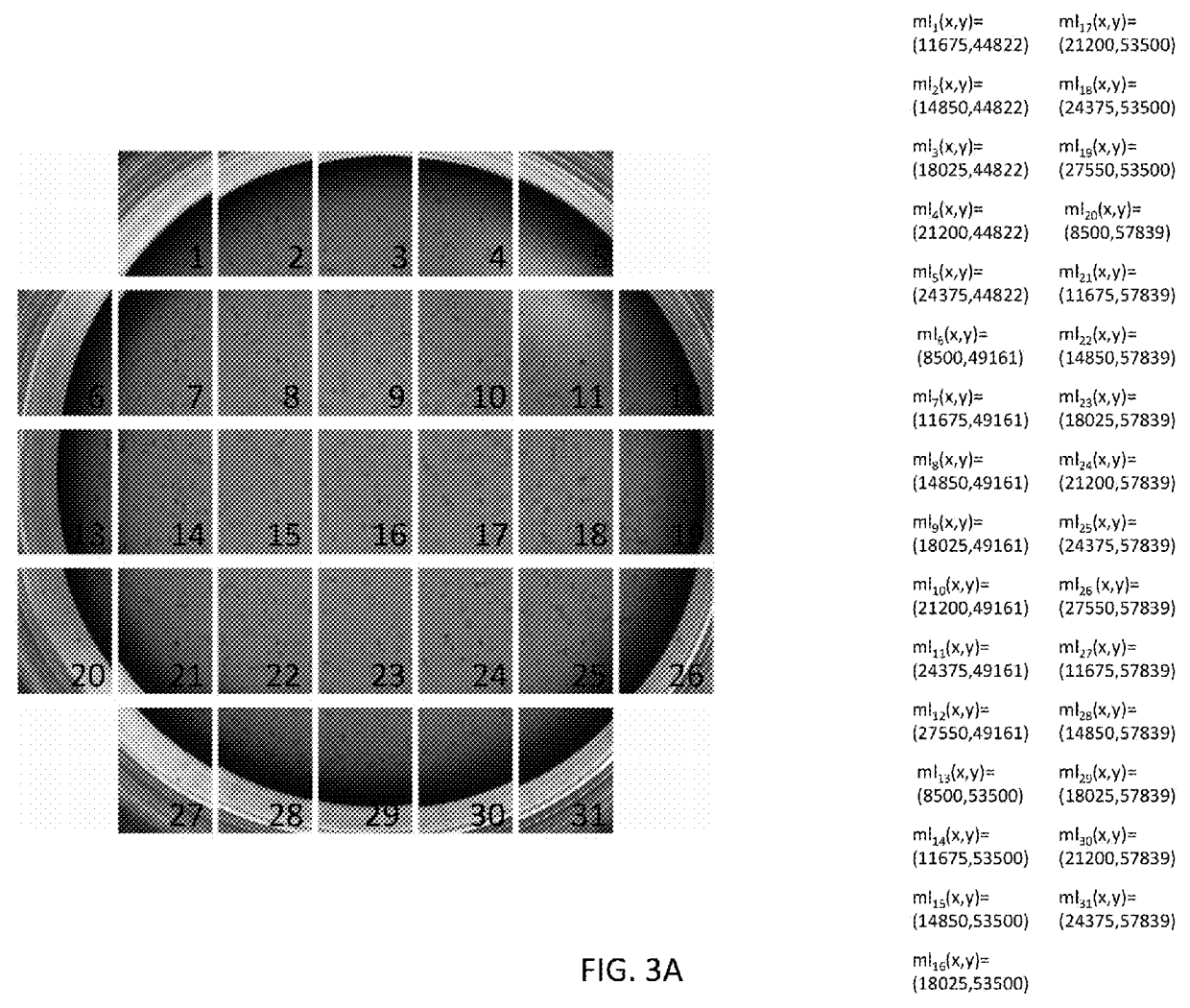
Figure 3B:
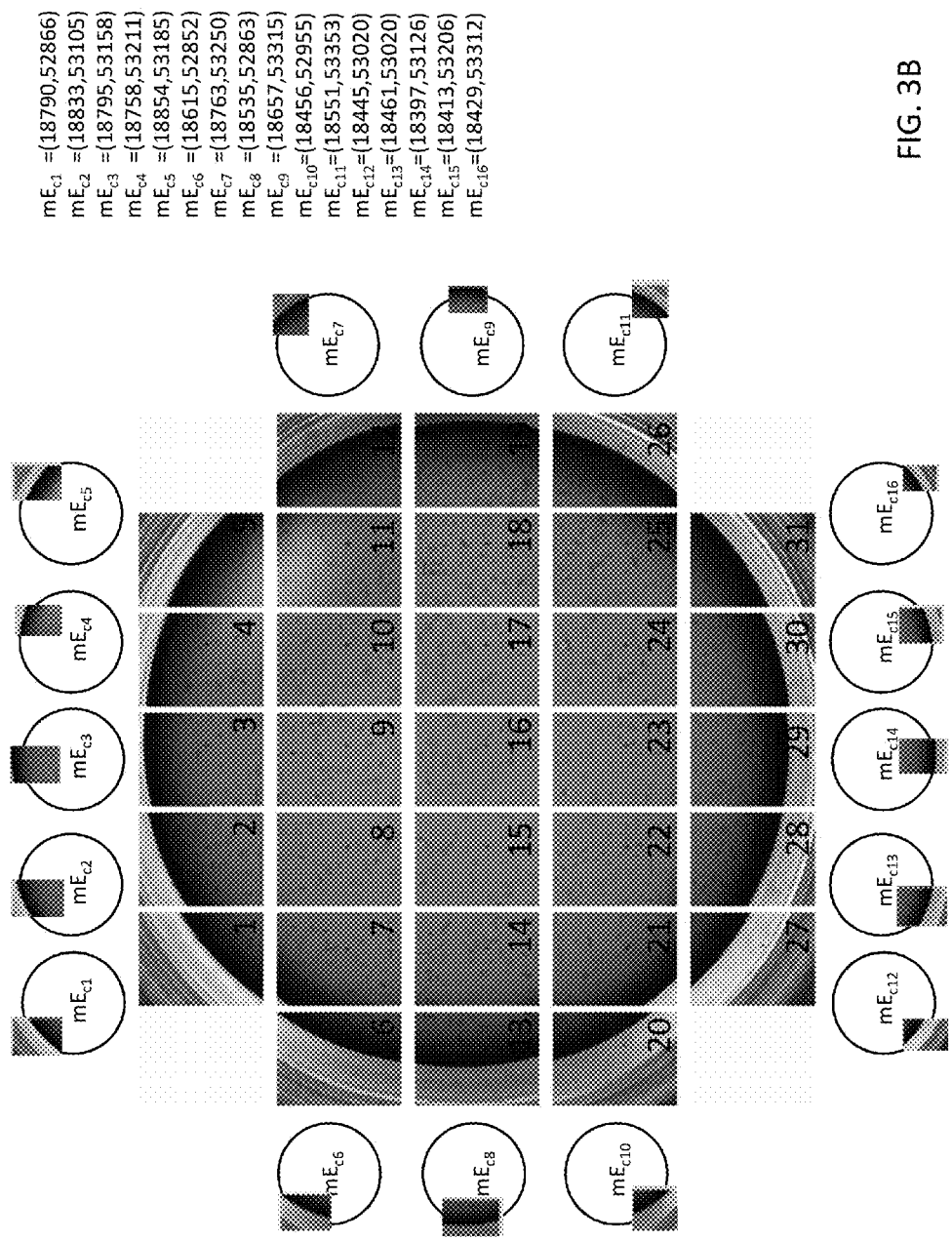
Figure 3C:
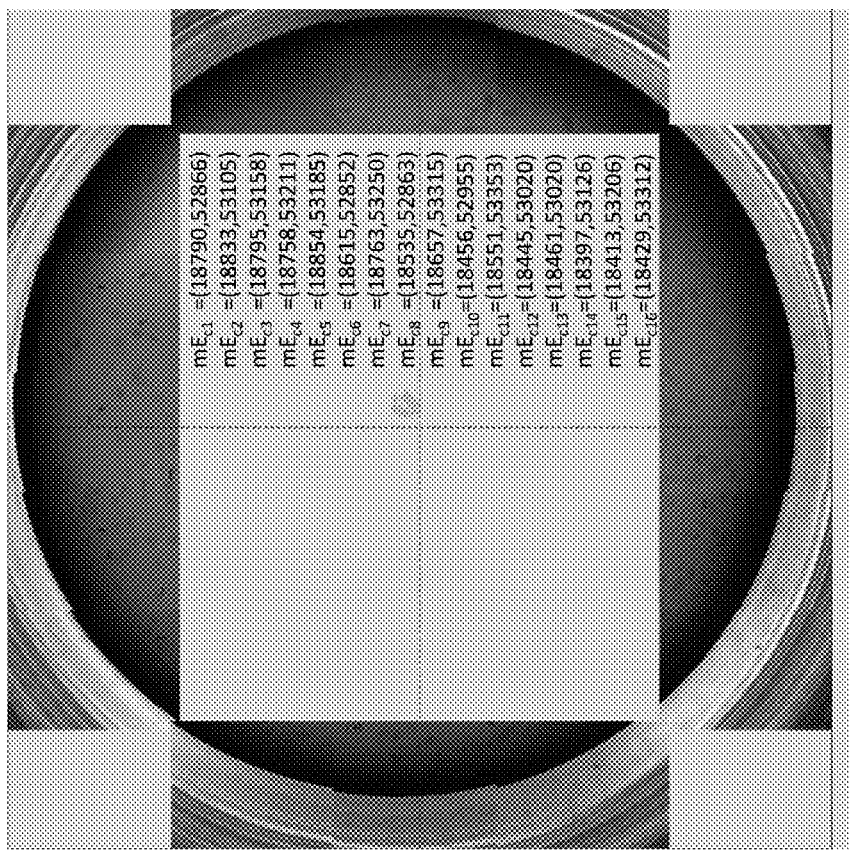

In some embodiments, the center of the well is calculated based on more than one image of the well. An exemplary method is illustrated in FIGS. 3A-3C. In FIG. 3A, a reconstruction of a single well based on 31 images is shown. To aid image reconstruction, the (x,y) coordinate for a designated region of each image (in this example, the coordinate of the top left corner) is listed.

In FIG. 3B, each image containing a well edge portion is analyzed. Each of these images contains an arc-shaped well edge portion due to the circular shape of the well. The arc shaped of each well edge portion is used to calculate an estimated center point for the entire well based on the shape of the arc in each image. Values derived from this exemplary set of images are provided in FIG. 3B. One of skill in the art may use similar methods for geometric well shapes other than circles. Each of the estimated center points from FIG. 3B are then averaged, as shown in FIG. 3C. This average value may be used as the calculated center of the well.

In some embodiments, the center of a first well is calculated, subsequently the center of a second well is calculated based on its relative distance to the first well center. For example, in some embodiments, e.g., a multiwell assay plate, the center of a first well of the assay plate is calculated, e.g., as described above. For any subsequent well of the same plate, a well center may be calculated, e.g., by a known relative distance between the well centers on the plate. This saves time and processing power.

In some embodiments, a position of an encoded microcarrier from the plurality is assigned according to a two-dimensional coordinate system, based on the one or more images, or data representative thereof (e.g., as shown in block 106). In some embodiments, the two-dimensional coordinate system is the same as the system used to represent the center of the well. In some embodiments, this assignment process is repeated for more than one microcarrier in the one or more images. In some embodiments, the position of the encoded microcarrier is assigned by one or more processors of the present disclosure.

In some embodiments, assigning the position of a microcarrier comprises transforming an image coordinate of the microcarrier to a two-dimensional well coordinate of the microcarrier according to a two-dimensional coordinate system of the present disclosure. For example, in some embodiments, an image of a well does not comprise the calculated center of the well (cf. the center of the well depicted in FIG. 3C and the 31 well images shown in FIGS. 3A and 3B). In this case, a single two-dimensional coordinate system is used to determine the distance between the microcarrier in the image and the calculated well center. As such, a coordinate system intrinsic to the well alone will not include the well center. Therefore, in some embodiments, a transformation is undertaken to convert the coordinate system of one or more microcarriers in the image (e.g., an image or frame coordinate) to the coordinate system of the well center (e.g., a two-dimensional well coordinate).

In some embodiments, calculating the center of a well comprises transforming the center of the well according to a two-dimensional coordinate system to a center of the well according to a pixel-based system. In some embodiments, assigning the position of the first encoded microcarrier further comprises transforming the position of the first encoded microcarrier according to the two-dimensional coordinate system to a position of the first encoded microcarrier according to the pixel-based system. In some embodiments, determining whether the distance between the position of the first encoded microcarrier and the center of the well exceeds a threshold distance further comprises comparing the threshold distance with the distance between the position of the first encoded microcarrier and the center of the well according to the pixel-based system. For example, the one or more images may comprise a plurality of pixels. The well center and/or the position of one or more microcarriers of the image may be converted to pixels or groups of pixels comprising the image. This may be advantageous, for example, in embodiments using a bright-field image to select a detection area (e.g., using the methods, systems, devices, and computer-readable storage media described herein) and a corresponding fluorescence image to detect an analyte. In this case, the position of a microcarrier in the bright-field image may correspond to the fluorescence reading (e.g., mean fluorescence intensity or MFI) associated with that microcarrier, allowing the user to measure analyte levels associated with each microcarrier in the detection area.

In some embodiments, a determination is made as to whether the distance between the position of an encoded microcarrier and the calculated center of the well exceeds a threshold distance (e.g., as shown in block 108). In some embodiments, the distance refers to squared Euclidean distance (e.g., according to a two-dimensional coordinate system). In some embodiments, the determination is made by one or more processors of the present disclosure. In some embodiments, in accordance with a determination that the distance between the position of an encoded microcarrier and the center of the well exceeds the threshold distance, the encoded microcarrier is excluded from the detection area (e.g., as shown in block 110). In some embodiments, in accordance with a determination that the distance between the position of an encoded microcarrier and the center of the well does not exceed the threshold distance, the encoded microcarrier is included in the detection area (e.g., as shown in block 112).

Figure 4:
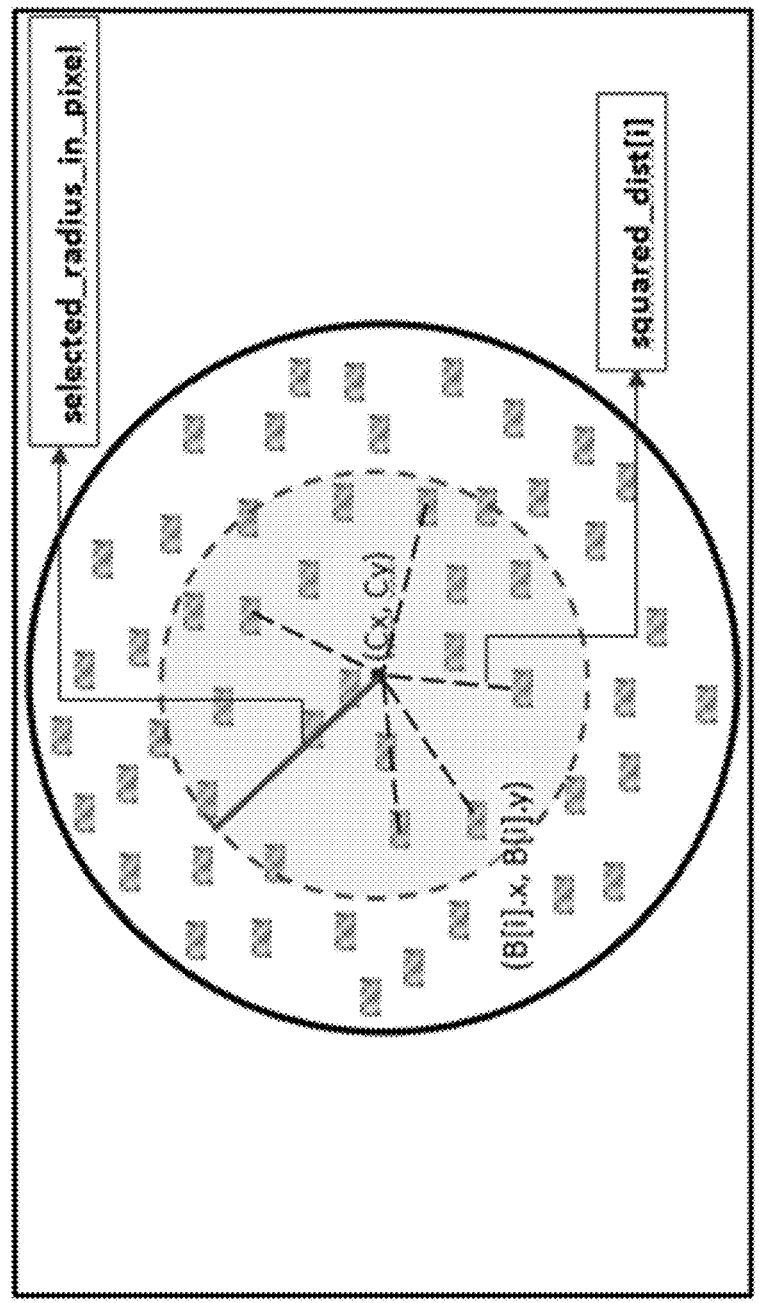
FIG. 4 shows a diagram for selecting detection area based on squared Euclidean distance in accordance with some embodiments.

FIG. 4 illustrates a determination of distance for multiple microcarriers, in accordance with some embodiments. A well image (e.g., constructed from one or more images of a well) is depicted with a plurality of microcarriers. The center of the well is depicted according to a two-dimensional coordinate system as "(Cx, Cy)." The distances between the well center and multiple microcarrier positions are depicted as dashed lines. An exemplary microcarrier position according to the two-dimensional coordinate system is shown as "(B[i].x, B[i].y)." The detection area is depicted as a shaded circle with a dashed perimeter. In this example using a circular well, the threshold distance serves as the radius of the detection area. Multiple microcarriers either included in or excluded from the detection area are depicted.

In some embodiments, a microcarrier code is decoded. Exemplary microcarrier codes and methods for decoding them are provided in section IV infra. In some embodiments, the microcarrier decoding occurs before the selection of a detection area. In some embodiments, the microcarrier decoding occurs with the selection of a detection area. In some embodiments, the microcarrier decoding occurs after the selection of a detection area. In some embodiments, only microcarriers included in the detection area are decoded. In other embodiments, microcarriers both within and outside of the detection area are decoded. For example, in some embodiments, microcarrier decoding is performed, then the detection area is selected. Subsequently, only microcarriers within the detection area are analyzed, even though all have been decoded. This may be advantageous, for example, if a user wishes to change the detection area; even if the detection area is subsequently expanded, all of the microcarriers will have been decoded.

In some embodiments, an amount of an analyte bound to an encoded microcarrier in the detection area is detected. Suitable detection agents and methods are described infra. In some embodiments, fluorescence detection is used. In some embodiments, luminescence detection is used.

In some embodiments, detecting an amount of analyte bound to a microcarrier comprises determining a unit of area for the microcarrier. For example, a microcarrier whose analyte level is being detected represents a certain unit of area within an image (e.g., a fluorescence image for a fluorescent detection agent). In this example, each microcarrier may be assigned a pixel radius, within which any fluorescence intensity (e.g., as represented by a pixel intensity, such as that obtained using a CCD camera of the present disclosure) is associated within the microcarrier. In some embodiments, the unit of area may be determined using the one or more images of the microcarriers (e.g., a bright-field image may be used to determine the dimensions and position of a microcarrier in a corresponding fluorescence image). In other embodiments, the unit of area may be designated (e.g., user- or system-designated) based on known or estimated microcarrier dimensions.

In some embodiments, data representing a user selection of the threshold distance are received. For example, a user may wish to select the threshold distance for the detection area. In some embodiments, the user inputs the threshold distance (e.g., in a unit of measurement such as a µm, or in pixels). In some embodiments, the user selects a desired level of variation (e.g., a CV %) in a parameter such as detected analyte levels (e.g., MFI), intrinsic fluorescence, and so forth. For example, a system or device of the present disclosure may determine a CV % based on the whole area within one or more images (e.g., based on detected MFI from a fluorescence image). If the CV % of the entire image area is greater than the user designated CV %, the detection area may be decreased iteratively until the CV % is within the user designated CV % range or value. Therefore, in this example, the user selects the threshold distance indirectly by specifying a CV % or range thereof, which the system or device of the present disclosure may use as a cutoff to determine the detection area. Considerations for selecting a detection area with respect to a microcarrier-based assay are further discussed in Example 1 below. In some embodiments, the threshold distance is one that results in a CV % of MFI that is less than about 15%, less than about 12%, less than about 10%, less than about 8%, or less than about 5%.

In some embodiments, the user selection may be received using one or more processors of the present disclosure coupled to an input device of the present disclosure (e.g., through use of a GUI in combination with a keyboard, mouse, touch-sensitive surface, and the like). In some embodiments, the user selection may be retrieved from a memory of the present disclosure.

In some embodiments, a depiction of at least a portion of the detection area is generated. For example, one or more images may be used to reconstruct a well image (see, e.g., FIGS. 7 and 8). The depiction may be a stylized image, or it may be an actual image (e.g., a bright-field image). In some embodiments, the depiction depicts one or more encoded microcarriers included in said detection area. For example, the included microcarrier(s) may be labeled or marked using a graphical or text-based indication (e.g., the squares shown in FIG. 8), or the detection area itself may be depicted (e.g., the dashed circles in FIG. 8), which illustrates to the user which microcarrier(s) are included.

Figure 8:
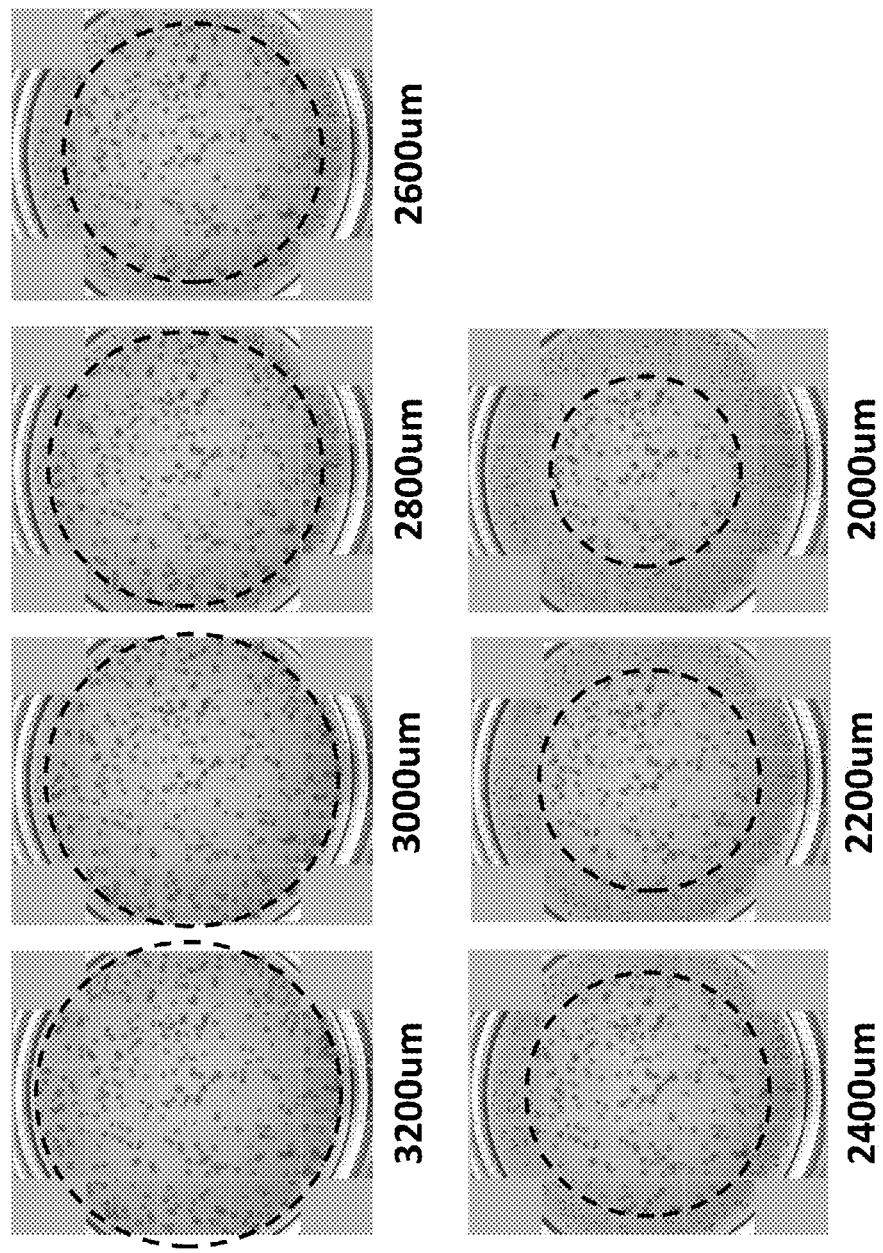
FIG. 8 shows different detection area sizes applied to an exemplary image of a well containing microcarriers. The detection area radius is provided for each image. In each image, microcarriers included in the detection area are outlined with a square; approximate detection areas are also depicted with dashed lines.

In some embodiments, the depiction further depicts a representation of one or more encoded microcarriers excluded from the detection area. In some embodiments, if the included microcarrier(s) are labeled or marked, then the excluded microcarrier(s) may lack the label or mark (e.g., as shown in FIG. 8 with the absence of a square), or may be indicated using a different label or mark. In some embodiments, the detection area itself may be depicted (e.g., the dashed circles in FIG. 8), which illustrates to the user which microcarrier(s) are excluded.

In some embodiments, the well comprises a biological sample that comprises the plurality of microcarriers. For example, the plurality of microcarriers may be contacting and/or submersed in the biological sample. In some embodiments, the biological sample comprises one or more analytes of interest. Further description of biological samples is provided infra.

IV. Encoded Microcarriers

Certain aspects of the present disclosure relate to encoded microcarriers. It will be appreciated by one of skill in the art that the methods and systems described herein may be suitable for use with a variety of encoded microcarriers. It is thought that the methods, devices, computer-readable storage media, systems described herein may be applied to any type of microcarrier that uses light-based detection.

In some embodiments, the encoded microcarrier is a light transmitted assay bead or digital magnetic microbead. Examples of such beads may be found, e.g., in U.S. Pat. Nos. 7,858,307; 7,871,770; 8,148,139; and U.S. PG Publication No. US20110007955. Other exemplary microcarriers suitable for use as described herein may be found, e.g., in PCT/IB2016/000937.

In some embodiments, the encoded microcarrier comprises a substantially transparent polymer layer having a first surface and a second surface, the first and the second surfaces being parallel to each other; a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code; and a capture agent for capturing an analyte, wherein the capture agent is coupled to at least one of the first surface and the second surface of the substantially transparent polymer layer in at least the center portion of the substantially transparent polymer layer. In some embodiments, the microcarrier further includes a second substantially transparent polymer layer aligned with and affixed to the first substantially transparent polymer layer. In some embodiments, the first and second substantially transparent polymer layers each have a center portion, and the center portions of both the first and second substantially transparent polymer layers are aligned. In some embodiments, the microcarrier further includes a magnetic, substantially non-transparent layer that encloses the center portions of both the first and second substantially transparent polymer layers. In some embodiments, the magnetic, substantially non-transparent layer is affixed between the first and second substantially transparent polymer layers. In some embodiments, the magnetic, substantially non-transparent layer is between the substantially non-transparent polymer layer and the center portions of both the first and second substantially transparent polymer layers. An exemplary microcarrier of this type, which includes some of the optional microcarrier aspects and features described herein, is illustrated in FIGS. 2A-2D.

Turning now to FIGS. 2A and 2B, an exemplary microcarrier 200 is shown. Microcarrier 200 includes substantially transparent polymer layer 202 and substantially non-transparent polymer layer 204. In addition, microcarrier 200 includes magnetic layer 206. As shown in FIG. 2A, magnetic layer 206 may be shaped as a ring between center portion 208 and substantially non-transparent layer 204.

FIG. 2B shows that magnetic layer 206 may be embedded within layer 202. Layer 202 may also include more than one layer, such that magnetic layer 206 is sandwiched between two substantially transparent polymer layers (e.g., as in FIG. 2B). Alternatively, magnetic layer 206 may be affixed to the same surface of layer 202 as layer 204, or magnetic layer 206 may be affixed to the surface of layer 202 opposite layer 204. In some embodiments, magnetic layer 206 may include nickel.

Magnetic layer 206 bestows magnetic properties onto microcarrier 200, which advantageously may be used for many applications. For example, microcarrier 200 may be affixed to a surface by magnetic attraction during a washing step, allowing for effective washing without losing or otherwise disrupting the microcarriers.

Figure 2D:
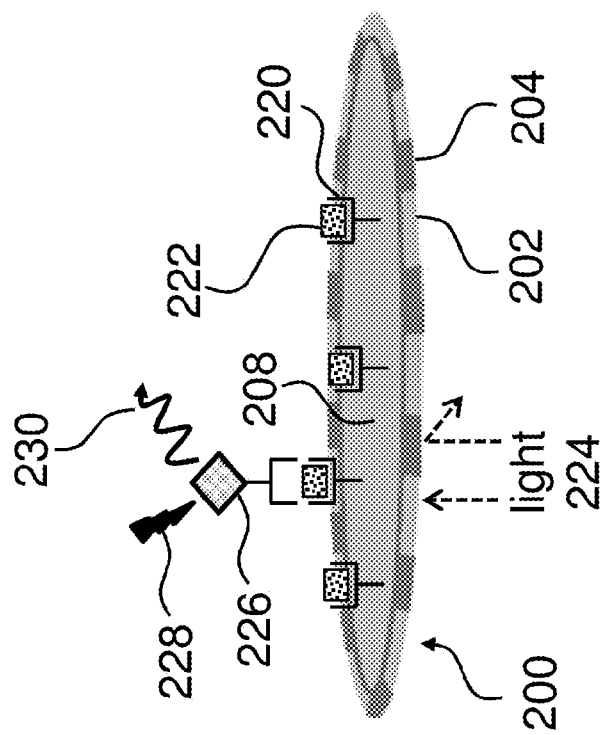
FIGS. 2C & 2D show an exemplary assay for analyte detection using an exemplary microcarrier.
Figure 2C:
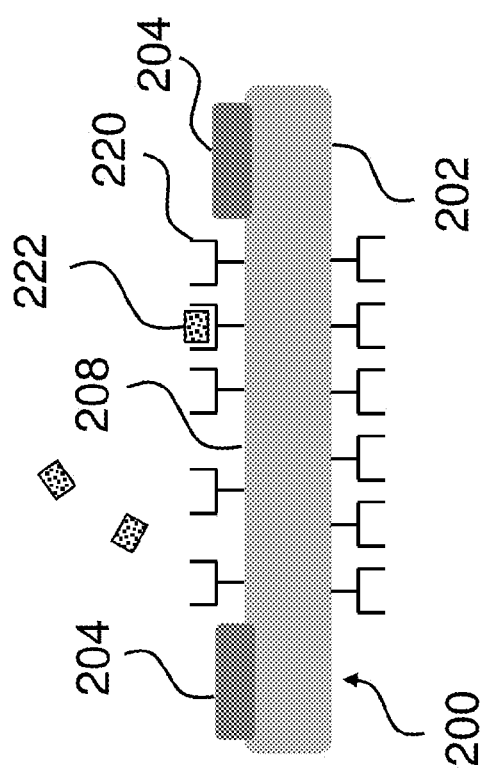

In addition to its magnetic properties, layer 206 is also substantially non-transparent. When imaged as shown in FIGS. 2C and 2D (described below), layer 206 will block, either in part or in whole, transmitted light, thereby creating a pattern for imaging. As shown in FIG. 2A, layer 206 is also asymmetric—in this example, it includes gap 210. This asymmetry creates an orientation indicator that can be imaged. Advantageously, an orientation indicator may be utilized during image recognition to orient the two-dimensional shape created by imaging layer 204 in a uniform orientation for easier analog code recognition. This allows microcarriers imaged in any orientation to be decoded.

FIGS. 2C and 2D show an exemplary assay using microcarrier 200 for analyte detection. FIG. 2C shows that microcarrier 200 may include capture agent 220 coupled to one or more surfaces in at least center portion 208. Microcarrier 200 is contacted with a solution containing analyte 222, which is captured by capture agent 220. As described herein, various capture agents may be used to capture different types of analytes, ranging from small molecules, nucleic acids, and proteins (e.g., antibodies) to organelles, viruses, and cells. FIG. 2C illustrates a single microcarrier species (i.e., microcarrier 200), which captures analyte 222, but in a multiplex assay multiple microcarrier species are used, each species having a particular capture agent that recognizes a specific analyte.

FIG. 2D illustrates an exemplary process for "reading" microcarrier 200, e.g., using the methods, systems, and/or devices described herein. This process includes two steps that may be accomplished simultaneously or separately. First, the capture of analyte 222 by capture agent 220 is detected. In the example shown in FIG. 2D, detection agent 226 binds to analyte 222. Analyte not captured by a capture agent coupled to microcarrier 200 may have been washed off prior to detection, such that only analytes bound to microcarrier 200 are detected. Detection agent 226 also includes a reagent for detection. As one example, detection agent 226 may include a fluorophore that, when excited by light 228 (e.g., supplied by excitation light 514 shown in FIG. 5A) at a wavelength within the excitation spectrum of the fluorophore, emits a photon such as light 230 (e.g., emitted light 518 in FIG. 5A). Light 230 may be detected by any suitable detection means, such as camera 510 (e.g., a CCD camera).

In addition, microcarrier 200 is read for its unique identifier. In the example shown in FIG. 2D, light 224 (e.g., supplied by bright-field light 508 shown in FIG. 5A) is used to illuminate the field containing microcarrier 200 (in some embodiments, light 224 may have a different wavelength than lights 228 and 230; for example, light 224 may be bright-field or white light). When light 224 illuminates the field containing microcarrier 200, it passes through substantially transparent polymer layer 202 but is blocked by substantially non-transparent polymer layer 204, as shown in FIG. 2D. This generates a light pattern that can be imaged, for example, by light microscopy (e.g., using bright-field microscopy). This light pattern is based on the two-dimensional shape (i.e., digital or analog code) of microcarrier 200. Standard image recognition techniques may be used to decode the analog code represented by the image of microcarrier 200, as described herein.

The analyte detection and identifier imaging steps may occur in any order, or simultaneously. Advantageously, both detection steps shown in FIG. 2D may be accomplished on one imaging device, such as the devices and systems of the present disclosure. As one example, a microscope capable of both fluorescence and light (e.g., bright field) microscopy may be used to quantify the amount of analyte 222 bound to microcarrier 200 (e.g., as detected by detection agent 226) and image the analog code created by layers 202 and 204. This allows for a more efficient assay process with fewer equipment requirements.

In some embodiments, the magnetic, substantially non-transparent layer is between about 50 nm and about 10 μm in thickness. In some embodiments, the thickness of the magnetic, substantially non-transparent layer is less than about any of the following thicknesses (in nm): 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100. In some embodiments, the thickness of the magnetic, substantially non-transparent layer is greater than about any of the following thicknesses (in nm): 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500. That is, the thickness of the magnetic, substantially non-transparent layer may be any of a range of thicknesses (in nm) having an upper limit of 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100 and an independently selected lower limit of 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500, wherein the lower limit is less than the upper limit.

In some embodiments, the magnetic, substantially non-transparent layer is about 0.1 μm in thickness. In some embodiments, the magnetic, substantially non-transparent layer is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm in thickness. In some embodiments, the thickness of the magnetic, substantially non-transparent layer is about 0.01 µm, about 0.02 µm, about 0.03 µm, about 0.04 µm, about 0.05 µm, about 0.06 µm, about 0.07 µm, about 0.08 µm, about 0.09 µm, about 0.1 µm, about 0.11 µm, about 0.12 µm, about 0.13 µm, about 0.14 µm, about 0.15 µm, about 0.16 µm, about 0.17 µm, about 0.18 µm, about 0.19 µm, about 0.20 µm, about 0.25 µm, about 0.30 µm, about 0.35 µm, about 0.40 µm, about 0.45 µm, or about 0.50 µm.

In some embodiments, the microcarrier further includes an orientation indicator for orienting the analog code of the substantially non-transparent polymer layer. Any feature of the microcarrier that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator may be independent of the substantially non-transparent polymer layer. For example, it may be formed as a part of a magnetic layer and/or substantially transparent polymer layer. In other embodiments, the orientation indicator may be formed as part of the substantially non-transparent polymer layer. In some embodiments, the orientation indicator comprises an asymmetry of the magnetic, substantially non-transparent layer.

In some embodiments, the microcarrier further includes one or more columns projecting from a surface of the microcarrier (e.g., the top and/or bottom surface of the microcarrier). As used herein, a "column" may refer to any geometric shape that projects from the microcarrier surface and does not necessarily denote any regularity in dimensions, nor any cylindrical character. For example, the outer surface of a column may or may not be parallel with the microcarrier surface. Examples of columnar shapes that may project from a microcarrier include without limitation a rectangular prism, a triangle, a pyramid, a cube, a cylinder, a sphere or half-sphere, a cone, and so forth. In some embodiments, the one or more columns are not within a center portion of the first and/or the second substantially transparent polymer layer. In some embodiments, the one or more columns may project from an outside-facing surface (e.g., a surface not affixed to another layer) of one or more of the first and the second substantially transparent polymer layers. It is to be noted that any descriptions of microcarrier thickness herein do not include the one or more columns in the stated dimensions. That is to say, microcarrier thickness as described herein is independent of any optional columns projecting therefrom.

In some embodiments, the one or more columns are between about 1 µm and about 10 µm tall. In some embodiments, the one or more columns are about 1 µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the one or more columns are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 µm and about 10 µm. In some embodiments, the one or more columns have a diameter of about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm. In some embodiments, the one or more columns have a diameter less than about any of the following lengths (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in µm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In other embodiments, the encoded microcarrier comprises a substantially non-transparent polymer layer having a first surface and a second surface, the first and the second surfaces being parallel to each other, wherein an outline of the substantially non-transparent polymer layer comprises a two-dimensional shape that represents an analog code; and a capture agent for capturing an analyte, wherein the capture agent is coupled to at least one of the first surface and the second surface of the substantially non-transparent polymer layer in at least a center portion of the substantially non-transparent polymer layer.

In some embodiments, the microcarrier further includes one or more columns projecting from a surface of the substantially non-transparent polymer layer. As described in greater detail supra, a "column" may refer to any geometric shape that projects from the microcarrier surface and does not necessarily denote any regularity in columnar dimension(s). Any of the exemplary columnar shapes described above may be used.

In some embodiments, the one or more columns are between about 1 µm and about 10 µm tall. In some embodiments, the one or more columns are about 1 µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the one or more columns are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 µm and about 10 µm. In some embodiments, the one or more columns have a diameter of about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm. In some embodiments, the one or more columns have a diameter less than about any of the following lengths (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in µm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In some embodiments, the microcarrier further includes a magnetic layer comprising a magnetic material affixed to a surface of the substantially non-transparent polymer layer. In some embodiments, the magnetic layer does not extend beyond the two-dimensional shape of the substantially non-transparent polymer layer. That is to say, if the outline of the substantially non-transparent polymer layer were to be imaged, the resulting image would not be altered by the presence or absence of the magnetic layer. In some embodiments, the magnetic layer may include the one or more columns described above. That is, the one or more columns described above may be made of a magnetic material described herein.

In some embodiments, the microcarrier further includes an orientation indicator for orienting the analog code of the substantially non-transparent polymer layer. Any feature of the microcarrier that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator comprises an asymmetry of the outline of the substantially non-transparent polymer layer. For example, the orientation indicator may comprise a visible feature, such as an asymmetry, of the outline of the microcarrier.

In some embodiments, a substantially transparent polymer of the present disclosure comprises an epoxy-based polymer. Suitable epoxy-based polymers for fabrication of the compositions described herein include, but are not limited to, the EPON™ family of epoxy resins provided by Hexion Specialty Chemicals, Inc. (Columbus, Ohio) and any number of epoxy resins provided by The Dow Chemical Company (Midland, Mich.). Many examples of suitable polymers are commonly known in the art, including without limitation SU-8, EPON 1002F, EPON 165/154, and a poly (methyl methacrylate)/poly(acrylic acid) block copolymer (PMMA-co-PAA). For additional polymers, see, for example, Warad, *IC Packaging: Package Construction Analysis in Ultra Small IC Packaging*, LAP LAMBERT Academic Publishing (2010); *The Electronic Packaging Handbook*, CRC Press (Blackwell, ed.), (2000); and Pecht et al., *Electronic Packaging Materials and Their Properties*, CCR Press, 1$^{st}$ ed., (1998). These types of materials have the advantage of not swelling in aqueous environments which ensures that uniform microcarrier size and shape are maintained within the population of microcarriers. In some embodiments, the substantially transparent polymer is a photoresist polymer. In some embodiments, the epoxy-based polymer is an epoxy-based, negative-tone, near-UV photoresist. In some embodiments, the epoxy-based polymer is SU-8.

In some embodiments, the substantially non-transparent polymer is a polymer described herein (e.g., SU-8) mixed with one or more non-transparent or colored dye(s). In other embodiments, the substantially non-transparent polymer is a black matrix resist. Any black matrix resist known in the art may be used; see, e.g., U.S. Pat. No. 8,610,848 for exemplary black matrix resists and methods related thereto. In some embodiments, the black matrix resist may be a photoresist colored with a black pigment, e.g., as patterned on the color filter of an LCD as part of a black matrix. Black matrix resists may include without limitation those sold by Toppan Printing Co. (Tokyo), Tokyo OHKA Kogyo (Kawasaki), and Daxin Materials Corp. (Taichung City, Taiwan).

In some embodiments, reference may be made to a center portion of one or more polymer layers. A center portion of the present disclosure may take any shape. In some embodiments, the shape of the center portion may reflect or correspond to the shape (e.g., outline) of the corresponding polymer layer. In other embodiments, the shape of the center portion may be independent of the shape (e.g., outline) of the corresponding polymer layer. For example, a center portion of a circular microcarrier surface may be circular in some embodiments and square in other embodiments. A center portion of a square microcarrier surface may be square in some embodiments and circular in other embodiments.

In some embodiments, a center portion of a polymer layer of the present disclosure is about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, or about 90% of the surface area of the polymer layer. In some embodiments, a center portion of a polymer layer of the present disclosure is less than about any of the following fractions of the substantially transparent polymer layer (in %): 90, 85, 80, 75, 70, 65, 60, 55, 50, 45, 40, 35, 30, 25, 20, 15, 10, or 7. In some embodiments, a center portion of a polymer layer of the present disclosure is greater than about any of the following fractions of the substantially transparent polymer layer (in %): 5, 7, 10, 15, 20, 25, 30, 35, 40, 45, 50, 55, 60, 65, 70, 75, 80, or 85. That is, the fraction of the polymer layer surface area included in the center portion may be any of a range of percentages having an upper limit of 90, 85, 80, 75, 70, 65, 60, 55, 50, 45, 40, 35, 30, 25, 20, 15, 10, or 7 and an independently selected lower limit of 5, 7, 10, 15, 20, 25, 30, 35, 40, 45, 50, 55, 60, 65, 70, 75, 80, or 85, wherein the lower limit is less than the upper limit. In some embodiments, the center portion of a polymer layer comprises about 25% of the surface area of the polymer layer. In some embodiments, a center portion of a microcarrier surface includes the entire surface minus an outline portion of the microcarrier.

As described above, a microcarrier of the present disclosure may further include a magnetic layer, which may adopt a variety of shapes as described herein. In some embodiments, the magnetic layer may be a substantially non-transparent layer. In some embodiments, the magnetic layer may comprise a magnetic material. A magnetic layer of the present disclosure may be made of any suitable magnetic material, such as a material with paramagnetic, ferromagnetic, or ferrimagnetic properties. Examples of magnetic materials include without limitation iron, nickel, cobalt, and some rare earth metals (e.g., gadolinium, dysprosium, neodymium, and so forth), as well as alloys thereof. In some embodiments, the magnetic material comprises nickel, including without limitation elemental nickel and magnetic nickel alloys such as alnico and permalloy. The inclusion of a magnetic layer in a microcarrier of the present disclosure may be advantageous, e.g., in facilitating magnetic separation, which may be useful for washing, collecting, and otherwise manipulating one or more microcarriers.

As described above, in some embodiments, the magnetic layer may be affixed to a surface of the substantially transparent polymer layer and enclose a center portion of the substantially transparent polymer layer. In other embodiments, as described above, the magnetic layer may include one or more columns; i.e., the one or more columns described above may be made of a magnetic material described herein.

In some embodiments, a microcarrier of the present disclosure may be encoded with a barcode or other digital code. For example, the microcarrier may have a digitally coded structure that is partially transmissive and opaque to light. The systems described herein may be used to transmit light through the barcode (e.g., using an objective, detection stage, and light source of the present disclosure), capture an image of the barcode (e.g., using a camera of the present disclosure), and decode the barcode image (e.g., using one or more processors of the present disclosure). Barcode decoding methods are commonly known in the art. Examples of barcode-encoded microcarriers may be found, e.g., in U.S. Pat. Nos. 7,858,307; 7,871,770; 8,148,139; and U.S. PG Publication No. US20110007955.

In other embodiments, a microcarrier of the present disclosure may be encoded with an analog code, such as a two-dimensional shape. For example, a microcarrier of the present disclosure may be encoded with a substantially non-transparent layer that constitutes a two-dimensional shape. For example, as described above, the two-dimensional shape may constitute the shape of a substantially non-transparent layer that contrasts with a substantially transparent layer of the microcarrier, or it may constitute the shape of the microcarrier itself (e.g., the perimeter). Any two-dimensional shape that can encompass a plurality of resolvable and distinctive varieties may be used. In some embodiments, the two-dimensional shape comprises one or more of linear, circular, elliptical, rectangular, quadrilateral, or higher polygonal aspects, elements, and/or shapes.

In some embodiments, the two-dimensional shape of the substantially non-transparent polymer layer comprises a gear shape. A gear shape as used herein may refer to a plurality of shapes (e.g., gear teeth) arrayed on the perimeter of a substantially round, elliptical, or circular body, where at least two of the shapes of the plurality are spatially separated. In some embodiments, the gear shape comprises a plurality of gear teeth. In some embodiments, the analog code is represented by one or more aspects selected from the height of one or more gear teeth of the plurality, the width of one or more gear teeth of the plurality, the number of gear teeth in the plurality, and the arrangement of one or more gear teeth within the plurality. Advantageously, a gear shape encompasses multiple aspects, including the height of gear teeth, the width of gear teeth, the number of gear teeth, and the arrangement of gear teeth, that may be varied in order to generate a large diversity of potential unique two-dimensional shapes. It is to be appreciated, however, that since the gear shapes of the present disclosure are used for encoding and are not required to physically intermesh with another gear (e.g., as with mechanical gears that transmit torque), gear teeth of the present disclosure are not constrained by the need for identical or intermeshing shapes, either within one gear shape or between multiple gear shapes. As such, the variety of shapes that may be considered a gear tooth of the present disclosure is significantly greater than with a mechanical gear.

In some embodiments, the plurality of gear teeth comprises one or more gear teeth that are between about 1 µm and about 10 µm wide. In some embodiments, the plurality of gear teeth comprises one or more gear teeth that are about 1 µm wide, about 1.5 µm wide, about 2 µm wide, about 2.5 µm wide, about 3 µm wide, about 3.5 µm wide, about 4 µm wide, about 4.5 µm wide, about 5 µm wide, about 5.5 µm wide, about 6 µm wide, about 6.5 µm wide, about 7 µm wide, about 7.5 µm wide, about 8 µm wide, about 8.5 µm wide, about 9 µm wide, about 9.5 µm wide, or about 10 µm wide. In some embodiments, the plurality of gear teeth comprises one or more gear teeth that are less than about any of the following widths (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following widths (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of widths having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the plurality of gear teeth comprises one or more gear teeth that are between about 1 µm and about 10 µm tall. In some embodiments, the plurality of gear teeth comprises one or more gear teeth that are about 1

µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the plurality of gear teeth comprises one or more gear teeth that are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. It is to be appreciated that a gear tooth may have different measurable heights, depending on the point of reference, if the adjacent perimeter segments from which the gear tooth extends are uneven.

In some embodiments, the plurality of gear teeth comprises one or more gear teeth that are spaced between about 1 µm and about 10 µm apart. In some embodiments, the plurality of gear teeth comprises one or more gear teeth that are spaced about 1 µm apart, about 1.5 µm apart, about 2 µm apart, about 2.5 µm apart, about 3 µm apart, about 3.5 µm apart, about 4 µm apart, about 4.5 µm apart, about 5 µm apart, about 5.5 µm apart, about 6 µm apart, about 6.5 µm apart, about 7 µm apart, about 7.5 µm apart, about 8 µm apart, about 8.5 µm apart, about 9 µm apart, about 9.5 µm apart, or about 10 µm apart. In some embodiments, the plurality of gear teeth comprises one or more gear teeth that are spaced less than about any of the following widths apart (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are spaced greater than about any of the following widths apart (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be spaced any of a range of widths apart having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

Analog-encoded microcarriers may be decoded, for example, by illuminating the microcarrier by passing light through the substantially transparent portions (e.g., substantially transparent polymer layer(s)) and/or the surrounding solution. The light may then fail to pass through, or pass through with a lower intensity or other appreciable difference, the substantially non-transparent portions (e.g., substantially non-transparent polymer layer(s)) of the microcarrier to generate an analog-coded light pattern corresponding to the microcarrier code. Decoding may employ any type of light microscopy, including without limitation one or more of: bright field, dark field, phase contrast, differential interference contrast (DIC), Nomarski interference contrast (NIC), Nomarski, Hoffman modulation contrast (HMC), or fluorescence microscopy. It will be appreciated by one of skill in the art that the decoding methods described herein may find use in decoding microcarriers in a multiplex assay, e.g., decoding two or more microcarriers or microcarrier species bearing different codes.

In certain embodiments, as described herein, the analog codes may be decoded using bright field microscopy, and analyte(s) may be detected using fluorescence microscopy. In some embodiments, decoding an analog code includes using analog shape recognition to identify the microcarrier. Conceptually, this decoding may involve imaging the analog code of each microcarrier (e.g., in a solution or sample), comparing each image against a library of analog codes, and matching each image to an image from the library, thus positively identifying the code. Optionally, as described herein, when using microcarriers that include an orientation indicator (e.g., an asymmetry), the decoding may further include a step of rotating each image to align with a particular orientation (based in part, e.g., on the orientation indicator). For example, if the orientation indicator includes a gap, the image could be rotated until the gap reaches a predetermined position or orientation (e.g., a 0° position of the image). In some embodiments, an image may be matched with an analog code (e.g., an image file from a library of image files, with each image file corresponding to a unique two-dimensional shape/analog code) within a predetermined threshold, e.g., that tolerates a predetermined amount of deviation or mismatch between the image and the exemplar analog code image. Such a threshold may be empirically determined and may naturally be based on the particular type of two-dimensional shapes used for the analog codes and the extent of variation among the set of potential two-dimensional shapes.

Various shape recognition software, tools, and methods are known in the art. Examples of such APIs and tools include without limitation Microsoft® Research FaceSDK, OpenBR, Face and Scene Recognition from ReKognition, Betaface API, and various ImageJ plugins. In some embodiments, the analog shape recognition may include without limitation image processing steps such as foreground extraction, shape detection, thresholding (e.g., automated or manual image thresholding), and the like.

In some embodiments, a microcarrier of the present disclosure is a substantially circular disc. As used herein, a substantially circular shape may refer to any shape having a roughly identical distance between all of the points of the shape's perimeter and the shape's geometric center. In some embodiments, a shape is considered to be substantially circular if the variation among any of the potential radii connecting the geometric center and a given point on the perimeter exhibit 10% or lesser variation in length. As used herein, a substantially circular disc may refer to any substantially circular shape wherein the thickness of the shape is significantly less than its diameter. For example, in some embodiments, the thickness of a substantially circular disc may be less than about 50%, less than about 40%, less than about 30%, less than about 20%, less than about 15%, less than about 10%, or less than about 5% of its diameter. In certain embodiments, the thickness of the substantially circular disc may about 20% of its diameter. It is to be appreciated that the microcarriers of the present disclosure whose outline is a gear shape may also be considered substantially circular discs; for example, the shape of the microcarrier excluding the one or more gear teeth may comprise a substantially circular disc.

In some embodiments, the microcarrier is less than about 200 µm in diameter. For example, in some embodiments, the diameter of the microcarrier is less than about 200 µm, less than about 180 µm, less than about 160 µm, less than about 140 µm, less than about 120 µm, less than about 100 µm, less than about 80 µm, less than about 60 µm, less than about 40 µm, or less than about 20 µm.

In some embodiments, the diameter of the microcarrier is about 180 µm, about 160 µm, about 140 µm, about 120 µm, about 100 µm, about 90 µm, about 80 µm, about 70 µm, about 60 µm, about 50 µm, about 40 µm, about 30 µm, about 20 µm, or about 10 µm. In certain embodiments, the microcarrier is about 60 µm in diameter.

In some embodiments, the microcarrier is less than about 50 µm in thickness. For example, in some embodiments, the thickness of the microcarrier is less than about 70 µm, about 60 µm, about 50 µm, about 40 µm, about 30 µm, less than about 25 µm, less than about 20 µm, less than about 15 µm, less than about 10 µm, or less than about 5 µm. In some embodiments, the thickness of the microcarrier is less than about any of the following thicknesses (in µm): 70, 65, 60, 55, 50, 45, 40, 35, 30, 25, 20, 15, 10, 9, 8, 7, 6, 5, 4, 3, or 2. In some embodiments, the thickness of the microcarrier is greater than about any of the following thicknesses (in µm): 1, 2, 3, 4, 5, 6, 7, 8, 9, 10, 15, 20, 25, 30, 35, 40, 45, 50, 55, 60, or 65. That is, the thickness of the microcarrier may be any of a range of thicknesses (in µm) having an upper limit of 70, 65, 60, 55, 50, 45, 40, 35, 30, 25, 20, 15, 10, 9, 8, 7, 6, 5, 4, 3, or 2 and an independently selected lower limit of 1, 2, 3, 4, 5, 6, 7, 8, 9, 10, 15, 20, 25, 30, 35, 40, 45, 50, 55, 60, or 65, wherein the lower limit is less than the upper limit.

In some embodiments, the thickness of the microcarrier is about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, or about 1 µm. In certain embodiments, the microcarrier is about 10 µm in thickness.

V. Systems, Devices, and Computer-Readable Storage Media for Selection of Detection Area Provided herein are systems, devices, and computer-readable storage media for selecting a detection area for a well comprising a plurality of encoded microcarriers. Any of the methods of the present disclosure may find use in one or more of the systems, devices, and computer-readable storage media described herein.

Figure 5B:
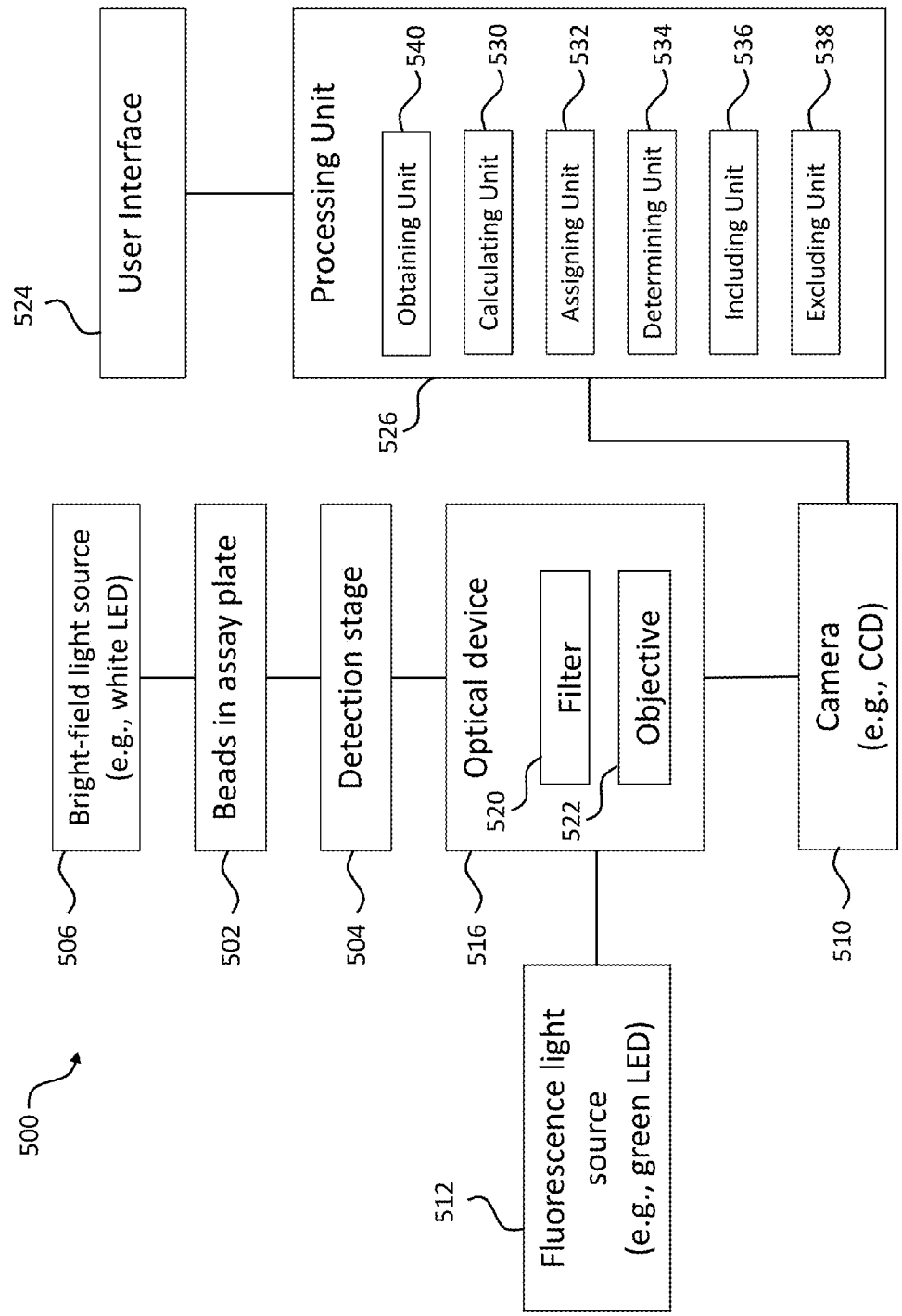

Attention is now directed to the functional block diagram of an exemplary system or device of the present disclosure shown in FIGS. 5A and 5B. FIG. 5A shows a functional block diagram depicting an exemplary configuration of an analyzing system or device in accordance with some embodiments. Assay plate 502 (e.g. a 96-well plate) is positioned on detection stage 504. In some embodiments, detection stage 504 is coupled to a stepper motor and/or controller (not shown) to allow assay plate 502 to be translated along the x/y axis (which is orthogonal to the z-axis depicted in FIG. 5A). Assay plate 502 includes a plurality of wells which are arranged in an array, for example, with 12 columns and 8 rows (not shown) for a 96-well plate. Bright-field light source 506 (e.g. white light LED) is configured to project light 508 transmitting through the well plate in the z-direction. The bottom of the well is typically transparent or translucent, allowing the light to pass through the microcarriers in the well and to be captured by camera 510 (e.g., a CCD camera). With bright-field light source 506, camera 510 is able to obtain a bright-field image useful for microcarrier decoding. In some embodiments, the resolution of camera 510's CCD sensor is sufficient to resolve the microcarrier code or pattern.

Fluorescence light source 512 is configured to project excitation light (e.g., light 514) to the bottom of the well to excite one or more fluorescence-based detection agents associated with the microcarriers. The wavelength of light emitted by fluorescence light source 512 may depend upon the excitation wavelength(s) of the one or more detection agent(s). In some embodiments, multiple fluorescence light sources may be used to excite multiple detection agents with distinct excitation wavelengths. Optical device 516 (e.g., including one or more filters 520, reflectors, mirrors, and/or objectives 522) is configured to guide excitation light 514 from fluorescence light source 512 to assay plate 502. Once excited by light 514, one or more detection agents associated with the microcarriers emit light 518, which is detected by camera 510.

Camera 510 is configured to obtain a bright-field image from light 508 and a fluorescence image from emitted light 518 for each well assay plate 502. In some embodiments, multiple fluorescence and/or bright-field images may be obtained from a single well, as exemplified infra. Camera 510 may include one or more lenses and may be movable along the Z-axis (e.g., coupled to one or more stepper motors and/or controllers) to align the focal plane with the bottom of the well so as to acquire a clear well image.

FIG. 5B shows another functional block diagram depicting an exemplary configuration of an analyzing system or device in accordance with some embodiments. Additional components are depicted. For example, additional, optional components of optical device 516 are shown, including filter 520 and objective 522. In some embodiments, filter 520 may comprise a filter block. In some embodiments, filter 520 may comprise one or more filters (e.g., an excitation filter and/or an emission or barrier filter), reflectors, and/or mirrors (e.g., a dichroic mirror or beam-splitter). In some embodiments, objective 522 may be an objective coupled to camera 510 for microscopic bright-field and/or fluorescence imaging. In some embodiments, objective 522 may be positioned above filter 520. In some embodiments, objective 522 may contain one or more lenses.

FIG. 5B also includes user interface 524 and processor 526. User interface 524 may be displayed on a computer monitor or other display to the user and may further comprise a GUI or other user interface to allow for user input (e.g., selection of a detection area size and/or threshold distance). Processor 526 may be used, e.g., to calculating a well center, assign a position of a microcarrier, determine whether a distance between the position of the first encoded microcarrier and the center of the well according to the two-dimensional coordinate system exceeds a threshold distance, and/or obtain data representing one or more well images. The components shown in FIGS. 5A and 5B are described in greater detail infra.

Figure 5C:
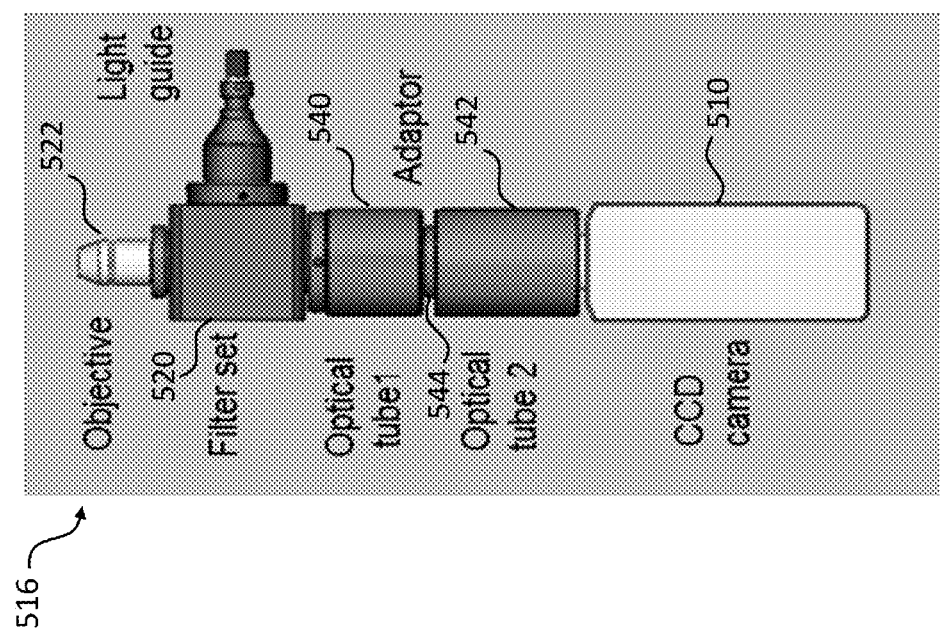
FIG. 5C illustrates an exemplary optical device for use in detection systems/devices in accordance with some embodiments.

FIG. 5C shows the components of exemplary optical device 516 in greater detail. Objective 522 may be used to transmit and/or focus lights 508, 514, and/or 518. Filter set 520 may contain one or more filters useful for, e.g., filtering excitation light 514 from emitted light 518. Optical device 516 may further include one or more optical tubes. In the example shown in FIG. 5C, optical device 516 has two optical tubes, 540 and 542, connected by adaptor 544. Optical device 516 also contains a CCD camera (e.g., camera 510).

Certain aspects of the present disclosure relate to assay plates comprising one or more wells (e.g., assay plate 502). The wells may be of any shape. Typically in the art, assay plate wells are circular. In principal, however, the methods of the present disclosure may be applied to any geometric well shape. In some embodiments, the assay plate wells are flat-bottomed to allow all or substantially all of the microcarriers therein to reside on a common focal plate in the Z-axis (e.g., as labeled in FIG. 5A).

Numerous assay plates are known in the art. For example, assay plates may include without limitation microplates such as 6-, 12-, 24-, 60-, 72-, 96-, 384-, or 1536-well plates. In some embodiments, the assay plate has a clear bottom (and a clear top, if a top is provided) for optical detection. Examples of suitable assay plates include without limitation clear polystyrene plates. Such plates are commercially available from Nunc™, Costar™ Corning®, Greiner Bio-One®, and the like.

Figure 7:
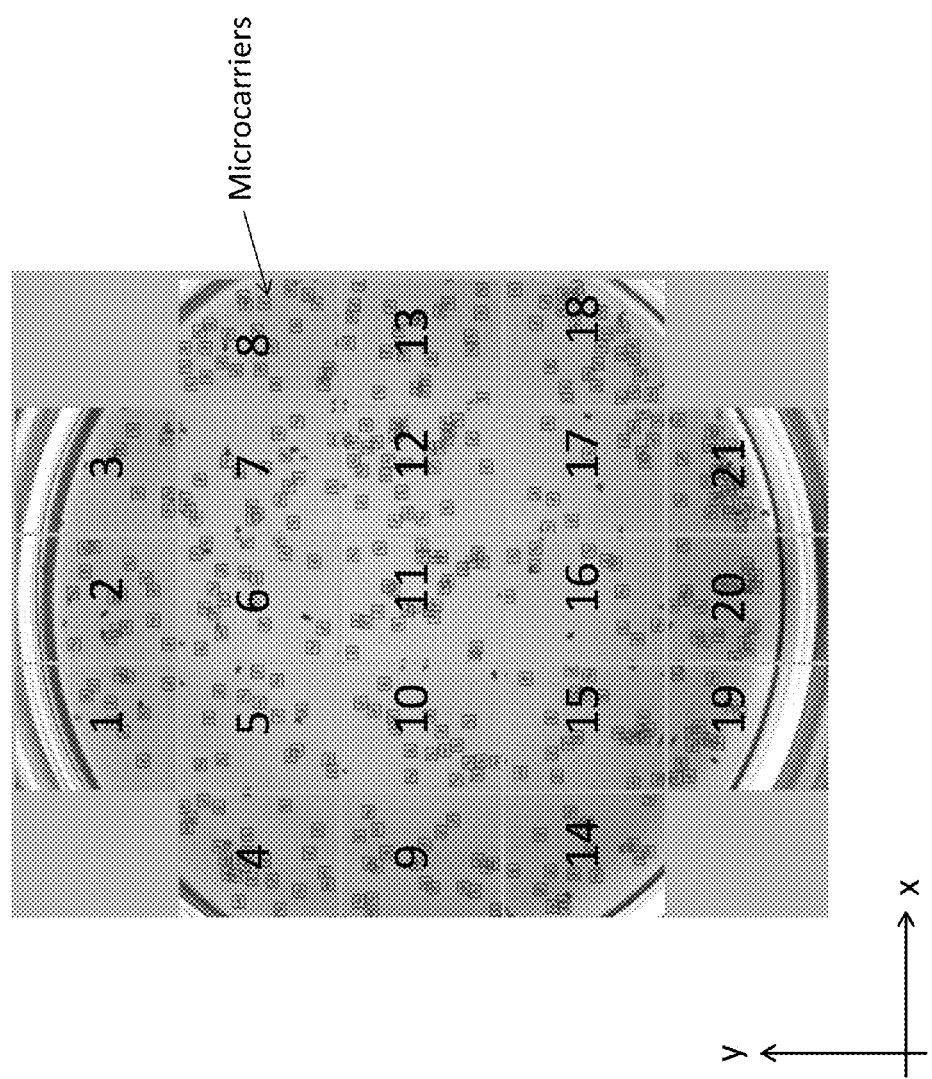
FIG. 7 shows an exemplary image of a well containing microcarriers. The x- and y-axes are labeled.

In some embodiments, the methods, systems, and devices of the present disclosure may include a detection stage (e.g., detection stage 504). A detection stage of the present disclosure may be used to position an assay plate of the present disclosure for imaging. In some embodiments, the assay plate rests atop the detection stage. In some embodiments, the detection stage is configured for an assay plate of particular dimensions, such as a standard 6-, 12-, 24-, 96-, 384-, or 1536-well plate. In some embodiments, the detection stage provides planar support and/or attachment to retain the assay plate in a fixed position during imaging. In some embodiments, the detection stage is open, or substantially transparent, in an area below one or more of the assay plate wells to allow for light transmission to the assay plate. In some embodiments, the detection stage is coupled to a motor (e.g., a stepper motor) that, through a controller, allows a device or system to manipulate the position of the assay plate in the x/y plane (e.g., as illustrated in FIG. 7). This allows the assay plate to be moved to capture images of different wells across the plate.

In some embodiments, the methods, systems, and devices of the present disclosure may include one or more light sources. In some embodiments, the methods, systems, and devices of the present disclosure include a light source suitable for bright-field imaging (e.g., bright-field light source 506). In some embodiments, a bright-field image of a well comprising a plurality of microcarriers is obtained using a bright-field light source, lens, and camera. For example, the assay plate containing a well with microcarriers may have substantially transparent top and/or bottom surfaces, such that the bright-field light source can illuminate the well for bright-field imaging. In certain embodiments, the assay plate further comprises a light diffuser film on one or both surfaces to homogenize the bright-field light (e.g., white light-emitting diode or LED). In some embodiments, a bright-field image of one or more microcarriers may be used to decode the digital or analog code. In some embodiments, the bright-field light source provides white light and may include, e.g., a white LED or tungsten-halogen lamp.

In some embodiments, the methods, systems, and devices of the present disclosure include a light source suitable for fluorescence imaging (e.g., fluorescence light source 512). In some embodiments, a fluorescence image of a well comprising a plurality of microcarriers is obtained using a fluorescence light source, lens, one or more filters, and camera. In some embodiments, fluorescence imaging is used to detect one or more analytes using one or more detection agents, as described infra. For example, in certain embodiments, bright-field imaging is used to decode the microcarriers, and fluorescence imaging is used to measure the amount of analyte bound to the microcarriers through a fluorescent detection agent. A variety of fluorescence light sources suitable for particular fluorophores are known in the art, including without limitation a mercury light source (e.g., a mercury arc lamp), a xenon light source (e.g., a xenon arc lamp), a metal halide light source (e.g., a metal halide arc lamp), and an LED. The particular fluorescence light source may depend upon which fluorophore is used; e.g., a red diode laser (665 nm), compact Argon Laser (488 nm) or green laser (530 nm) are commonly used for fluorescence light sources for variety of fluorophores (e.g., phycoerythrin (PE), Cy3, Cy5, and so forth).

In some embodiments, the methods, systems, and devices of the present disclosure include one or more filters (e.g., filter 520). For example, one or more filters may be used to separate excitation light (e.g., light 514) generated by a fluorescence light source from light emitted from a fluorophore-based detection agent (e.g., light 518). Typically, such filters may be present in a filter block or cube, which may contain elements such as an excitation filter (which filters light outside of the excitation wavelengths from reaching the detection agent associated with the microcarriers), an emission or barrier filter (which removes light other than that emitted from the detection agent associated with the microcarriers from reaching the camera), and a dichroic mirror or beam-splitter (which isolates the emission light traveling to the objective/camera from the excitation and other light sources).

In some embodiments, the methods, systems, and devices of the present disclosure include a camera (e.g., camera 510). In some embodiments, the camera is able to obtain images of the microcarrier code and of the detection agent signal. For example, in certain embodiments, the camera obtains a bright-field image (which may be used for microcarrier decoding and/or couting) and a fluorescence image (which may be used for analyte quantification through a fluorescent detection agent). In certain embodiments, the camera obtains a bright-field image (which may be used for microcarrier decoding and/or couting) and a luminescence image (which may be used for analyte quantification through a luminescent detection agent). Examples of suitable cameras include without limitation a charge-coupled device (CCD) camera.

In some embodiments, the methods, systems, and devices of the present disclosure include one or more processors (e.g., processor 526). Processor 526 and/or user interface 524 may be part of or coupled to a computer system, such as a laptop, desktop, or tablet computer. Other computer components may include, without limitation, a display or monitor, input devices such as a keyboard, mouse, trackpad, touch-sensitive surface (e.g., a touch-sensitive display), volatile memory (e.g., random access memory or RAM), non-volatile memory read only memory or ROM, flash memory, optical drive, magnetic storage devices such as a hard drive, etc.), an operating system, basic input/output system (BIOS), a system bus that couples system components including the memory to the one or more processors. For example, a system bus may be any of several types of bus structures including a memory bus or memory controller, a peripheral bus, and a local bus using any of a variety of bus architectures, including without limitation industry Standard Architecture (USA) bus, Micro Channel Architecture (MCA) bus, Enhanced ISA (EISA) bus, Video Electronics Standards Association (VESA) local bus, and Peripheral Component interconnect (PCI) bus.

The system memory may include non-transitory computer-readable storage media in the form of volatile and/or nonvolatile memory, e.g., such as ROM and/or RAM. A BIOS may containing basic routines that help to transfer information between elements within the computer system, such as during start-up, and is typically stored in ROM. RAM typically contains data and/or program modules that are immediately accessible to and/or presently being operated on by the one or more processors. The system memory may further include an operating system and/or one or more programs or applications accessible to the user through the operating system. Such programs or applications may be used, e.g., to execute one or more steps of the methods described herein.

A computer system may also include other removable/non-removable, volatile/nonvolatile non-transitory computer-readable storage media. These computer-readable storage media may include, without limitation, a hard disk that reads from or writes to non-removable, nonvolatile magnetic media, a magnetic disk drive that reads from or writes to a removable, nonvolatile magnetic disk, an optical disk drive that reads from or writes to a removable, nonvolatile optical disk such as a CD-ROM or other optical media, flash memory devices or drives, digital versatile disks, digital video tape, solid state RAM, solid state ROM, and the like. A hard disk drive is typically connected to the system bus through a non-removable memory interface, and a magnetic disk drive and/or optical disk drive are typically connected to the system bus by a removable memory interface. These and other devices are often connected to the one or more processors through an input interface that is coupled to the system bus, but may be connected by other interface and bus structures, such as a parallel port, game port or a universal serial bus (USB). In particular, a USB may be used to read from or write to a removable memory device, such as a flash drive. In addition, a computer system may operate in a network environment, such as a local area network (LAN), connected wirelessly or via Ethernet cable to a router or switch.

Figure 6:
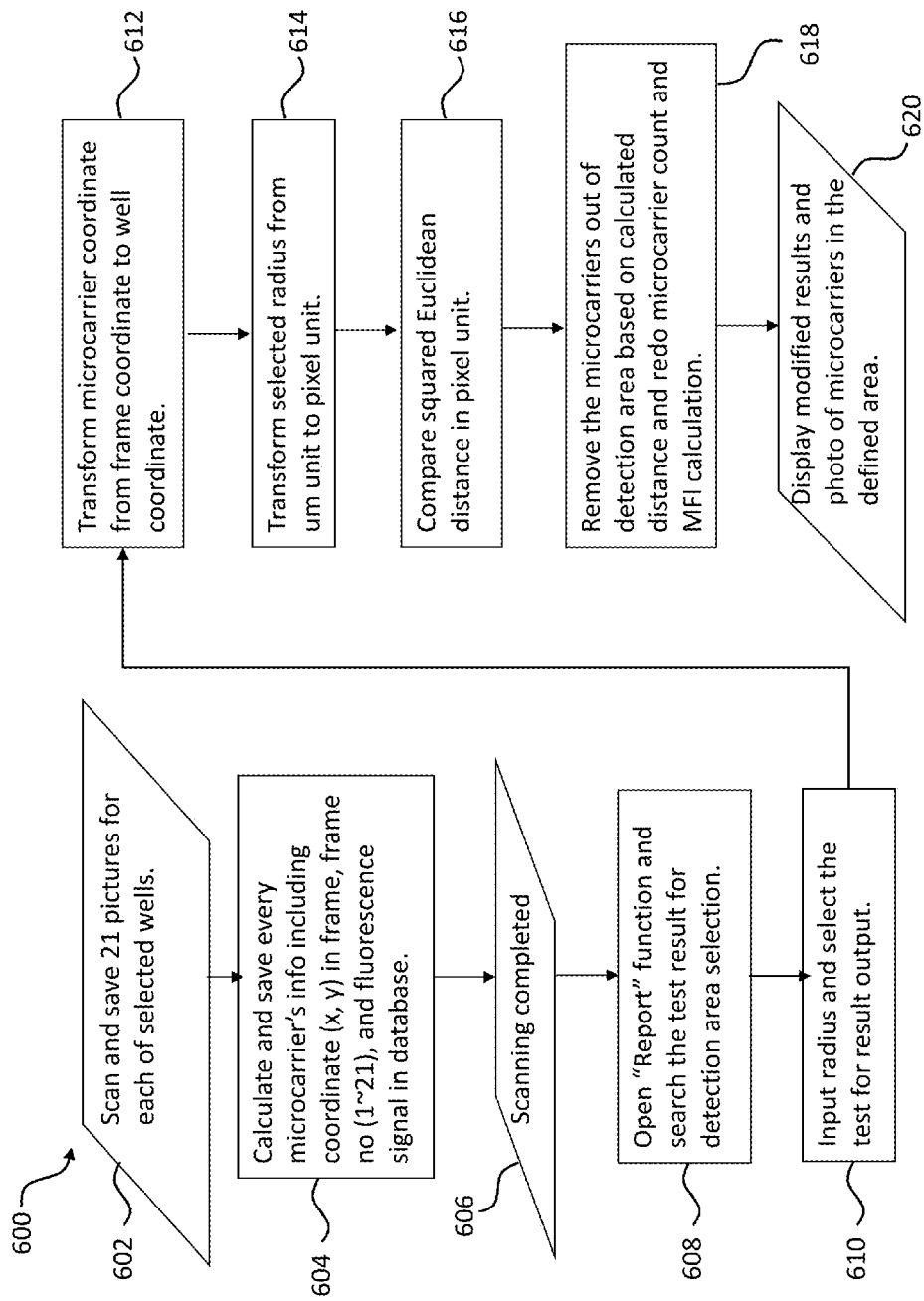
FIG. 6 is a flow diagram illustrating a method for selection of detection area in accordance with some embodiments.

In accordance with some embodiments, FIG. 6 provides a flow chart of exemplary method 600 that may be operated, e.g., using one or more of the systems, devices, and/or computer-readable storage media described herein, alone or in combination. At block 602, selected wells are each scanned and imaged into 21 images (e.g., bright-field images). This may be accomplished, e.g., using bright-field light source 506, assay plate 502, detection stage 504 (optionally coupled to a stepper motor), optical device 516, camera 510, and/or processor 526. These images may be saved in a memory of the present disclosure. At block 604, information for each microcarrier in the images is calculated and saved, such as the assigned two-dimensional position, frame or image number, and detected analyte level (e.g., fluorescence signal, intensity, or MFI), e.g., using processor 526 and a memory of the present disclosure. At block 606, the scanning is completed. At block 608, a "Report" function is opened (e.g., using an application instructing processor 526 to complete one or more method steps of the present disclosure), and the test results are searched for selection of detection area. At block 610, a user inputs a threshold distance (e.g., a radius for the detection area). At block 612, each microcarrier coordinate (from block 604) is converted from a frame or image coordinate to a well coordinate. At block 614, the user designated threshold distance or radius is converted from a unit of measurement to a pixel-based unit. At block 616, the squared Euclidean distance between the well center and the assigned position of each microcarrier is compared according to a pixel-based unit system. At block 618, microcarriers excluded from the detection area are removed based on the results from block 616, and optionally one or more parameters determined in block 604 (e.g., microcarrier count and/or MFI calculation) are updated (e.g., to exclude microcarriers outside of the detection area). At block 620, updated or modified results based on the designated threshold distance or radius are displayed (e.g., using a GUI of the present disclosure), and a photo or other depiction of the detection area is displayed and/or saved.

It will be appreciated by one of skill in the art that one or more of the components depicted in FIGS. 5A and 5B may be used to perform one or more of the steps depicted in the flow diagrams shown in FIGS. 1 and 6. For example, processor 526 may be used to implement one or more of the processes shown in blocks 104, 106, 108, 110, 112, 604, 608, 612, 614, 616, and/or 618. Light source 506, optical device 516 (optionally including filter 520 and/or objective 522), and camera 510 (optionally in combination with processor 526) may be used to implement one or more of the processes shown in blocks 102 and/or 602. Light source 512, optical device 516 (optionally including filter 520 and/or objective 522), and camera 510 (optionally in combination with processor 526) may be used to implement one or more of the processes shown in block 604 (e.g., detecting a fluorescence signal). These and other potential implementations will be readily evident to the skilled artisan.

In some embodiments, a non-transitory computer-readable storage medium of the present disclosure contains one or more programs for execution by one or more processors of a device of the present disclosure. In some embodiments, the device may include one or more processors of the present disclosure. In some embodiments, the device may include one or more processors, an objective, a camera, a light source, and/or a detection stage of the present disclosure. In some embodiments, the one or more programs include instructions which, when executed by one or more processors, cause a device of the present disclosure to perform any of the methods described herein. For example, in some embodiments, the instructions, when executed by the one or more processors, cause the device to: obtain data representing one or more images of a well of an assay plate positioned on the detection stage (the well comprises a plurality of encoded microcarriers); calculate a center of the well, according to a two-dimensional coordinate system, based on the obtained data; assign a position, according to the two-dimensional coordinate system, of a first encoded microcarrier from the plurality of encoded microcarriers based on the obtained data; determine whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude the first encoded microcarrier from a detection area; and in accordance with a determination that the distance between the position of the first encoded microcarrier and the center of the well does not exceed the threshold distance: include the first encoded microcarrier in the detection area, thereby selecting the detection area. In some embodiments, the data representing the one or more images of the well are obtained by a camera using an objective and a light source.

In some embodiments, a device of the present disclosure (e.g., an electronic imaging device) comprises a processing unit (e.g., one or more processors of the present disclosure). Exemplary processing unit 526 is illustrated in FIG. 5B. In some embodiments, processing unit 526 is coupled to a camera (e.g., camera 510), a light source (e.g., bright-field light source 506 and/or fluorescence light source 512), an objective (e.g., objective 522), and/or a detection stage (e.g., detection stage 504). In some embodiments, processing unit 526 is configured to: obtain (e.g., using obtaining unit 540) data representing one or more images of a well of an assay plate positioned on a detection stage, wherein the well comprises a plurality of encoded microcarriers; calculate (e.g., using calculating unit 530) a center of the well, according to a two-dimensional coordinate system, based on the obtained data; assign (e.g., using assigning unit 532) a position, according to the two-dimensional coordinate system, of a first encoded microcarrier from the plurality of encoded microcarriers based on the obtained data; determine (e.g., using determining unit 534) whether a distance between the position of the first encoded microcarrier and the center of the well according to the two-dimensional coordinate system exceeds a threshold distance; in accordance with a determination that the distance between the position of the first encoded microcarrier and the center of the well exceeds the threshold distance: exclude (e.g., using excluding unit 538) the first encoded microcarrier from a detection area; and in accordance with a determination that the distance between the position of the first encoded microcarrier and the center of the well does not exceed the threshold distance: include (e.g., using including unit 536) the first encoded microcarrier in the detection area, thereby selecting the detection area. In some embodiments, the data representing one or more images are obtained (e.g., using obtaining unit 540) by objective 522, light source 506 or 512, and camera 510. In some embodiments, processing unit 526 is coupled to a display. In some embodiments, the display may be configured to display user interface 524 (e.g., a GUI of the present disclosure). In some embodiments, user interface 524 may be used to receive data representing a user selection of a threshold distance of the present disclosure. It will be understood that a processing unit of the present disclosure may be configured to perform any of the methods of the present disclosure (e.g., using non-transitory computer-readable storage medium of the present disclosure) and/or may be configured for use in one or more devices of the present disclosure. Further, it will be understood that although processing unit 526 is shown in FIG. 5B as being coupled to a camera, light source, detection stage, and optical device, these is merely an optional configuration. In some embodiments, processing unit 526 and/or user interface 524 may be part of a stand-alone computer, laptop, tablet, smart phone, or the like that is configured to receive data from an optical device with a camera, light source, and detection stage, e.g., from a volatile or non-volatile non-transitory computer-readable storage medium, an optical disk drive, a removable memory device such as a flash memory device or drive, a magnetic disk drive, a network connection such as a wireless LAN or router, and so forth.

VI. Multiplex Assays

Certain aspects of the present disclosure relate to methods, systems, devices, and computer-readable storage media for selecting a detection area for a well comprising a plurality of encoded microcarriers suitable for use in multiplex assays. Such assays may involve, e.g., detecting analytes in a solution by using an encoded microcarrier, such as those described herein. In some embodiments, the solution comprising one or more encoded microcarriers (or microcarrier species) and one or more analytes is contained within a well of an assay plate of the present disclosure.

Exemplary multiplex assays of the present disclosure may comprise contacting a solution comprising a first analyte and a second analyte with a plurality of microcarriers, where the plurality of microcarriers comprises at least a first microcarrier of the present disclosure that specifically captures the first analyte and is encoded with a first code, and a second microcarrier of the present disclosure that specifically captures the second analyte and is encoded with a second code; decoding the first code and the second code using analog shape recognition to identify the first microcarrier and the second microcarrier; and detecting an amount of the first analyte bound to the first microcarrier and an amount of the second analyte bound to the second microcarrier. As described supra, a code of the present disclosure may be a digital code, such as a barcode, or the code may be an analog code, such as a two-dimensional shape.

In some embodiments, the multiplex assays of the present disclosure include contacting a solution comprising a first analyte and a second analyte with a plurality of microcarriers. In some embodiments, the plurality of microcarriers may include a first subset of one or more microcarriers of the present disclosure that specifically recognize the first analyte (e.g., using a capture agent, coupled to each microcarrier, that is specific for the first analyte), where each microcarrier of the first subset of the one or more microcarriers is encoded with a first code; and a second subset of one or more microcarriers of the present disclosure that specifically recognize the second analyte (e.g., using a capture agent, coupled to each microcarrier, that is specific for the second analyte), where each microcarrier of the second subset of the one or more microcarriers is encoded with a second code different from the first code.

In some embodiments, the first and second analytes may be different. That is to say, the second capture agent may specifically recognize a second analyte that is different from the first analyte. In other embodiments, the first and second analytes may be the same, e.g., the first and second microcarriers may both specifically recognize the same analyte (this may be useful, e.g., for quality control purposes), or they may recognize distinct regions of the same analyte (e.g., antibodies recognizing different epitopes of the same antigen).

The methods of the present disclosure may be used to detect analytes in any suitable solution. In some embodiments, the solution comprises a biological sample. Examples of biological samples include without limitation blood, urine, sputum, bile, stool, cerebrospinal fluid, interstitial fluid of skin or adipose tissue, saliva, tears, bronchial-alveolar lavage, oropharyngeal secretions, intestinal fluids, cervico-vaginal or uterine secretions, and seminal fluid. In some embodiments, the biological sample may be from a human. In other embodiments, the solution comprises a sample that is not a biological sample, such as an environmental sample, a sample prepared in a laboratory (e.g., a sample containing one or more analytes that have been prepared, isolated, purified, and/or synthesized), a fixed sample (e.g., a formalin-fixed, paraffin-embedded or FFPE sample), and so forth.

In some embodiments, the analysis is multiplexed, that is, each solution (e.g., a sample) is analyzed so that a signal from the signal emitting entity is detected by the reaction detection system for at least 2 analytes of interest, at least 3 analytes of interest, at least 4 analytes of interest, at least 5 analytes of interest, at least 10 analytes of interest, at least 15 analytes of interest, at least 20 analytes of interest, at least 25 analytes of interest, at least 30 analytes of interest, at least 35 analytes of interest, at least 40 analytes of interest, at least 45 analytes of interest, or at least 50 analytes of interest, or more.

In some aspects, a microcarrier of the present disclosure can comprise a capture agent. In some embodiments, the capture agent for a particular microcarrier species may be a "unique capture agent," e.g., a capture agent is associated with a particular microcarrier species having a particular identifier (e.g., analog code). The capture agent can be any biomolecule or a chemical compound capable of binding one or more analytes (such as a biomolecule or chemical compound) present in the solution. Examples of biomolecule capture agents include, but are not limited to, a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. Examples of chemical compound capture agents include, but are not limited to, individual components of chemical libraries, small molecules, or environmental toxins (for example, pesticides or heavy metals).

In some embodiments, the capture agent is coupled to a surface of the microcarrier (in some embodiments, in at least a center portion of the microcarrier surface). In some embodiments, the capture agent can be chemically attached to the microcarrier. In other embodiments, the capture agent can be physically absorbed to the surface of the microcarrier. In some embodiments, the attachment linkage between the capture agent and the microcarrier surface can be a covalent bond. In other embodiments, the attachment linkage between the capture agent and the microcarrier surface can be a non-covalent bond including, but not limited to, a salt bridge or other ionic bond, one or more hydrogen bonds, hydrophobic interactions, Van der Waals force, London dispersion force, a mechanical bond, one or more halogen bonds, aurophilicity, intercalation, or stacking.

In some aspects, more than one (such as two, three, four, five, six, seven, eight, nine, or ten) capture agents for the same analyte can each be associated with a microcarrier described herein. In this embodiment, each capture agent for a particular analyte binds to the analyte with a different affinity as measured by the dissociation constant of analyte/capture agent binding. Accordingly, within a plurality of microcarriers in a composition, there can be two or more subpopulations of microcarriers with capture agents that bind to the same analyte, but wherein the capture agents associated with each subpopulation bind to the analyte with a different affinity. In some embodiments, the dissociation constant of the analyte for any of the capture agents is not greater than $10^{-6}$M, such as $10^{-7}$M or $10^{-8}$M. In other embodiments, the dissociation constant of the analyte for any of the capture agents is from about $10^{-10}$ M to about $10^{-6}$M, such from about $10^{-10}$ M to about $10^{-7}$M, about $10^{-10}$ M to about $10^{-8}$M, about $10^{-10}$ M to about $10^{-9}$M, about $10^{-9}$ M to about $10^{-6}$M, about $10^{-9}$ M to about $10^{-7}$M, about $10^{-9}$ M to about $10^{-8}$M, about $10^{-8}$ M to about $10^{-6}$M, or about $10^{-8}$ M to about $10^{-7}$M. In some embodiments, the dissociation constant of the analyte for any two capture agents differs by as much as about 3 $\log_{10}$, such as by as much as about 2.5 $\log_{10}$, 2 $\log_{in}$, 1.5 $\log_{10}$, or 1 $\log_{10}$.

In some embodiments, an analyte of the present disclosure is coupled to a microcarrier for the capture of one or more analytes. In some embodiments, the one or more analytes may be captured from a sample, such as a biological sample described herein. In some embodiments, an analyte may include without limitation a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In other embodiments, the analyte is a chemical compound (such as a small molecule chemical compound) capable of binding to the capture agent such as individual components of chemical libraries, small molecules, or environmental toxins (for example, pesticides or heavy metals).

In some aspects, the analytes in a sample (such as a biological sample) can be labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radioisotope based, including, but not limited to, molecules labeled with $^{32}$P, $^{33}$P, $^{22}$Na, $^{36}$Cl, $^{2}$H, $^{3}$H, $^{35}$S, and $^{123}$I. In other embodiments, the signal-emitting entity is light-based including, but not limited to, luciferase (e.g., chemiluminescence-based), horseradish peroxidase, alkaline phosphatase, and derivatives thereof. In some embodiments, the biomolecules or chemical compounds present in the sample can be labeled with the signal-emitting entity prior to contact with the microcarrier. In other embodiments, the biomolecules or chemical compounds present in the sample can be labeled with the signal-emitting entity subsequent to contact with the microcarrier.

In some embodiments, the methods include detecting an amount of the first analyte bound to the first microcarrier and an amount of the second analyte bound to the second microcarrier. Any suitable analyte detection technique(s) known in the art may be used. For example, in some embodiments, the first and the second microcarriers may be incubated with one or more detection agents. In some embodiments, the one or more detection agents bind the first analyte captured by the first microcarrier and the second analyte captured by the second microcarrier. In some embodiments, the methods further include measuring the amount of detection agent bound to the first and the second microcarriers.

In some embodiments, the analytes in a solution (such as a biological sample) can be labeled with a detection agent (e.g., a signal-emitting entity) capable of emitting a detectable signal upon binding to the capture agent. In some embodiments, the detection agent can be colorimetric based. In other embodiments, the detection agent can be fluorescence-based including, but not limited to, phycoerythrin, blue fluorescent protein, green fluorescent protein, yellow fluorescent protein, cyan fluorescent protein, and derivatives thereof. In other embodiments, the detection agent can be radioisotope based, including, but not limited to, molecules labeled with $^{32}$P, $^{33}$P, $^{22}$Na, $^{36}$Cl, $^{2}$H, $^{3}$H, $^{35}$S, and $^{123}$I. In other embodiments, the detection agent is luminescence- or light-based, including, but not limited to, luciferase (e.g. chemiluminescence-based), horseradish peroxidase, alkaline phosphatase and derivatives thereof. In some embodiments, the biomolecules or chemical compounds present in the solution can be labeled with the detection agent prior to contact with the microcarrier composition. In other embodiments, the biomolecules or chemical compounds present in the solution can be labeled with the detection agent subsequent to contact with the microcarrier composition. In yet other embodiments, the detection agent may be coupled to a molecule or macromolecular structure that specifically binds the analyte of interest, e.g., a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and/or an antibody fragment.

In some embodiments, the detection agent is a fluorescent detection agent, and the amount of detection agent bound to the first and the second microcarriers is measured by fluorescence microscopy (e.g., a fluorescent microscope or plate reader). In other embodiments, the detection agent is a luminescent detection agent, and the amount of detection agent bound to the first and the second microcarriers is measured by luminescence microscopy (e.g., a luminescent microscope or plate reader).

In some embodiments, each analyte/capture agent may be used with a specific detection agent. As non-limiting examples, the detection agent may be a detection agent (e.g., a fluorescent, luminescent, enzymatic, or other detection agent) coupled to an antibody that specifically binds the analyte; or a ligand or receptor of a ligand-receptor pair, if the analyte is a cognate ligand/receptor of the ligand-receptor pair. This technique is conceptually similar to a sandwich ELISA or protein microarray that includes a capture and a detection antibody (though it should be noted in the present case that the agents in this example are not strictly limited to antibodies). As another non-limiting example, the detection agent may be a fluorescent or other detectable probe coupled to a protein of interest, such as a labeled analyte of interest. For example, a reaction may be used to couple detection agent(s) to one or more proteins in a solution of interest (e.g., a sample), which would then be captured by the capture agents (conceptually similar to an antigen capture-type of protein microarray).

In other embodiments, multiple unique analytes/capture agents may be used with a universal detection agent. As non-limiting examples, the detection agent may be an agent that binds to the Fc region of an antibody, if the analyte is an antibody; a fluorescent or other detectable probe coupled to an oligonucleotide (e.g., a single stranded oligonucleotide that hybridizes with an analyte), if the analyte is a polynucleotide such as DNA or RNA. The later scenario is conceptually similar to a microarray technique.

In some embodiments, the multiplex assays of the present disclosure may include one or more washing steps, e.g., to reduce contaminants, remove any substances non-specifically bound to the capture agent and/or microcarrier surface, and so forth. In some embodiments, a magnetic separation step may be used to wash a microcarrier containing a magnetic layer or material of the present disclosure. In other embodiments, other separation steps known in the art may be used. In some embodiments, the washing and/or separation steps may occur before analyte detection and/or detection area selection.

In some embodiments, the decoding step(s) may occur after the detecting step(s). In other embodiments, the decoding step(s) may occur before the detecting step(s). In still other embodiments, the decoding step(s) may occur simultaneously with the detecting step(s).

EXAMPLES

The following Example illustrates exemplary embodiments methods for selecting a detection area for a well comprising a plurality of encoded microcarriers (e.g., in a multiplex assay) that may find use, inter alia, in the systems, devices, and computer-readable storage media described herein. It is to be noted that these exemplary embodiments are in no way intended to be limiting but are provided to illustrate some of the aspects and features set forth herein.

Example 1: Selecting a Detection Area for a Well Containing Encoded Microcarriers The methods for selecting detection area described above were tested using a microcarrier reader similar in configuration to the exemplary system shown in FIGS. 5A and 5B and using encoded microcarriers similar in configuration to the exemplary microcarriers shown in FIGS. 2A-2D. The surface of these "blank" microcarriers was coated with non-reactive probes.

The reader was used to obtain both bright field and fluorescence images of multiple wells on a 96-well plate. Each well contained a population of microcarriers. For each well, 21 fluorescence and 21 corresponding bright field images were obtained. A reconstruction of an exemplary well based on 21 bright field images is shown in FIG. 7.

To observe the effect of detection area on fluorescence readings, the fluorescence images from seven wells of the 96-well plate were analyzed using different detection areas. The fluorescent signal detected was from the surface of the "blank" microcarriers coated with non-reactive probes. FIG. 8 shows a reconstruction of an exemplary well from these experiments. In each well image in FIG. 8, microcarriers that were included in the detection area are outlined with squares. Seven different detection area sizes were analyzed, with radii ranging from 2000-3200 μm. A fluorescence intensity measurement was performed for each microcarrier in the detection area. Table 1 below provides the variation of fluorescence readings (expressed as the coefficient of variation, or CV %, of the mean fluorescence intensity, or MFI) from each detection area. Table 2 below provides the microcarrier count within each detection area.

TABLE 1

Variation of MFI from different detection area sizes (CV %).

| | Detection area radius (μm) | | | | | | |
|---|---|---|---|---|---|---|---|
| well | 3200 | 3000 | 2800 | 2600 | 2400 | 2200 | 2000 |
| B2 | 12.6 | 9.3 | 7.5 | 5.8 | 4.6 | 4.7 | 5.0 |
| C2 | 15.6 | 9.4 | 8.4 | 6.5 | 5.0 | 4.3 | 4.5 |
| D2 | 11.5 | 9.7 | 7.3 | 4.6 | 3.8 | 3.9 | 4.1 |
| E2 | 11.9 | 9.7 | 6.8 | 4.5 | 3.7 | 3.5 | 3.6 |
| F2 | 12.8 | 10.7 | 8.1 | 4.6 | 3.5 | 2.9 | 2.5 |
| G2 | 11.7 | 9.2 | 8.3 | 5.5 | 4.0 | 3.1 | 3.0 |
| H2 | 11.4 | 8.6 | 6.7 | 4.8 | 3.5 | 3.6 | 3.0 |

TABLE 2

Bead count from different detection area sizes.

| | Detection area radius (μm) | | | | | | |
|---|---|---|---|---|---|---|---|
| well | 3200 | 3000 | 2800 | 2600 | 2400 | 2200 | 2000 |
| B2 | 159 | 144 | 129 | 108 | 86 | 73 | 54 |
| C2 | 159 | 144 | 130 | 105 | 87 | 69 | 51 |
| D2 | 138 | 116 | 106 | 85 | 65 | 50 | 41 |
| E2 | 142 | 125 | 106 | 91 | 80 | 72 | 57 |
| F2 | 134 | 115 | 102 | 87 | 78 | 62 | 50 |
| G2 | 141 | 132 | 121 | 99 | 85 | 72 | 59 |
| H2 | 144 | 128 | 114 | 98 | 81 | 67 | 48 |

These results demonstrate that the methods of the present disclosure were effective in reducing the CV % of fluorescence readings by two-thirds, from between 11.4% and 15.6% to less than 5%. This greatly reduces the variability of the fluorescence readings, thereby enhancing the overall accuracy and reproducibility of the assay.

In summary, the methods described herein allow the user to find a balance between sample size (e.g., number of beads measured) and sample variation (e.g., CV %) for any multiplex assay. Factors that may influence the balance between sample size and variation may include, e.g., concentration of microcarriers in an assay, number of different microcarrier species in a multiplex assay (e.g., higher number of species leads to fewer microcarriers of each species represented in each image or well), robustness of detection for each analyte (which may depend upon the affinity between the capture agent and the analyte, signal:noise ratio for each detection agent, analyte concentration, etc.), and so forth. Once a desired balance of these parameters has been found, these methods also allow for the uniform application of these parameters across multiple assays.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A system comprising:
an objective, a camera, a light source, a detection stage, one or more processors, a memory, and one or more programs stored in the memory, wherein the one or more programs are configured to be executed by the one or more processors, and wherein the one or more programs include instructions for:
obtaining data representing one or more images of a well of an assay plate positioned on the detection stage, wherein the well comprises a plurality of encoded microcarriers, wherein the plurality of encoded microcarriers comprises (i) a first subset of one or more encoded microcarriers, wherein each microcarrier of the first subset comprises a first code and a first capture agent that specifically recognizes a first analyte; and (ii) a second subset of one or more encoded microcarriers, wherein each microcarrier of the second subset comprises a second code and a second capture agent, wherein the second code is different from the first code, and wherein the data representing the one or more images of the well are obtained by the camera using the objective and the light source;
calculating a center of the well, according to a two-dimensional coordinate system, based on the obtained data;
assigning a position, according to the two-dimensional coordinate system, of a first encoded microcarrier from the plurality of encoded microcarriers based on the obtained data;
determining whether a distance between the position of the first encoded microcarrier and the center of the well according to the two-dimensional coordinate system exceeds a threshold distance;
in accordance with a determination that the distance between the position of the first encoded microcarrier and the center of the well exceeds the threshold distance:
excluding the first encoded microcarrier from a detection area; and
in accordance with a determination that the distance between the position of the first encoded microcarrier and the center of the well does not exceed the threshold distance:
including the first encoded microcarrier in the detection area, thereby selecting the detection area.

2. The system of claim 1, wherein the one or more programs further include instructions for decoding a code of the first encoded microcarrier.

3. The system of claim 1, wherein the one or more programs further include instructions for:
in accordance with the determination that the distance between the position of the first encoded microcarrier and the center of the well does not exceed the threshold distance, detecting an amount of an analyte bound to the first encoded microcarrier in the detection area.

4. The system of claim 3, wherein detecting the amount of the analyte bound to the first encoded microcarrier comprises detecting an amount of fluorescence in the position of the first encoded microcarrier.

5. The system of claim 3, wherein detecting the amount of the analyte bound to the first encoded microcarrier comprises detecting an amount of luminescence in the position of the first encoded microcarrier.

6. The system of claim 1, wherein the first encoded microcarrier comprises:
(a) a substantially transparent polymer layer having a first surface and a second surface, the first and the second surfaces being parallel to each other;
(b) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code;
(c) a capture agent for capturing an analyte, wherein the capture agent is coupled to at least one of the first surface and the second surface of the substantially transparent polymer layer in at least the center portion of the substantially transparent polymer layer;
(d) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and
(e) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers.

7. The system of claim 1, wherein the second capture agent specifically recognizes a second analyte that is different from the first analyte.

8. The system of claim 1, wherein the second capture agent specifically recognizes the first analyte.

9. The system of claim 1, wherein the one or more programs further include instructions for:
receiving data representing a user selection of the threshold distance.

10. The system of claim 1, wherein the one or more images of the well comprises a plurality of images of the well, wherein the plurality of images of the well comprises at least one well image that does not comprise the calculated center of the well, wherein the first microcarrier is represented in the at least one well image that does not comprise the calculated center of the well, and wherein assigning the position of the first microcarrier comprises transforming an image coordinate of the first microcarrier to a two-dimensional well coordinate of the first microcarrier according to the two-dimensional coordinate system.

11. The system of claim 1, wherein calculating the center of the well further comprises transforming the center of the well according to the two-dimensional coordinate system to a center of the well according to a pixel-based system;
wherein assigning the position of the first encoded microcarrier further comprises transforming the position of the first encoded microcarrier according to the two-dimensional coordinate system to a position of the first encoded microcarrier according to the pixel-based system; and
wherein determining whether the distance between the position of the first encoded microcarrier and the center of the well exceeds a threshold distance further comprises comparing the threshold distance with the distance between the position of the first encoded microcarrier and the center of the well according to the pixel-based system.

12. The system of claim 1, wherein the one or more programs further include instructions for:
generating a depiction of at least a portion of the detection area, the depiction depicting one or more encoded microcarriers included in said detection area.

13. The system of claim 12, wherein the depiction further depicts a representation of one or more encoded microcarriers excluded from the detection area.

14. The system of claim 1, wherein the well is a circular well.

15. The system of claim 1, wherein the well further comprises a biological sample comprising the plurality of encoded microcarriers.

16. A non-transitory computer-readable storage medium comprising one or more programs for execution by one or more processors of a device with an objective, a camera, a light source, and a detection stage, the one or more programs including instructions which, when executed by the one or more processors, cause the device to:
obtain data representing one or more images of a well of an assay plate positioned on the detection stage, wherein the well comprises a plurality of encoded microcarriers, wherein the plurality of encoded microcarriers comprises (i) a first subset of one or more encoded microcarriers, wherein each microcarrier of the first subset comprises a first code and a first capture agent that specifically recognizes a first analyte; and (ii) a second subset of one or more encoded microcarriers, wherein each microcarrier of the second subset comprises a second code and a second capture agent, wherein the second code is different from the first code, and wherein the data representing the one or more images of the well are obtained by the camera using the objective and the light source;
calculate a center of the well, according to a two-dimensional coordinate system, based on the obtained data;
assign a position, according to the two-dimensional coordinate system, of a first encoded microcarrier from the plurality of encoded microcarriers based on the obtained data;
determine whether a distance between the position of the first encoded microcarrier and the center of the well according to the two-dimensional coordinate system exceeds a threshold distance;
in accordance with a determination that the distance between the position of the first encoded microcarrier and the center of the well exceeds the threshold distance:
exclude the first encoded microcarrier from a detection area; and
in accordance with a determination that the distance between the position of the first encoded microcarrier and the center of the well does not exceed the threshold distance:
include the first encoded microcarrier in the detection area, thereby selecting the detection area.

17. An electronic imaging device comprising:
an objective,
a camera,
a light source,
a detection stage, and
a processing unit, the processing unit coupled to the objective, the camera, the light source, and the detection stage, the processing unit configured to:
obtain, using the objective, the light source, and the camera, data representing one or more images of a well of an assay plate positioned on the detection stage, wherein the well comprises a plurality of encoded microcarriers, wherein the plurality of encoded microcarriers comprises (i) a first subset of one or more encoded microcarriers, wherein each microcarrier of the first subset comprises a first code and a first capture agent that specifically recognizes a first analyte; and (ii) a second subset of one or more encoded microcarriers, wherein each microcarrier of the second subset comprises a second code and a second capture agent, and wherein the second code is different from the first code;
calculate a center of the well, according to a two-dimensional coordinate system, based on the obtained data;
assign a position, according to the two-dimensional coordinate system, of a first encoded microcarrier from the plurality of encoded microcarriers based on the obtained data;
determine whether a distance between the position of the first encoded microcarrier and the center of the well according to the two-dimensional coordinate system exceeds a threshold distance;
in accordance with a determination that the distance between the position of the first encoded microcarrier and the center of the well exceeds the threshold distance:
exclude the first encoded microcarrier from a detection area; and
in accordance with a determination that the distance between the position of the first encoded microcarrier and the center of the well does not exceed the threshold distance:
include the first encoded microcarrier in the detection area, thereby selecting the detection area.

* * * * *